(12) United States Patent
Kirsch et al.

(10) Patent No.: US 7,361,388 B2
(45) Date of Patent: *Apr. 22, 2008

(54) LIQUID-CRYSTALLINE COMPOUNDS HAVING A TETRAHYDROPYRAN RING

(75) Inventors: Peer Kirsch, Kanagawa (JP); Eike Poetsch, Muehltal (DE); Atsutaka Manabe, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 196 days.

This patent is subject to a terminal disclaimer.

(21) Appl. No.: 10/558,209

(22) PCT Filed: May 24, 2004

(86) PCT No.: PCT/EP2004/005539

§ 371 (c)(1),
(2), (4) Date: Nov. 25, 2005

(87) PCT Pub. No.: WO2004/106460

PCT Pub. Date: Dec. 9, 2004

(65) Prior Publication Data

US 2006/0289829 A1 Dec. 28, 2006

(30) Foreign Application Priority Data

May 27, 2003 (DE) ............... 103 24 311

(51) Int. Cl.
*C09K 19/34* (2006.01)
*C09K 19/12* (2006.01)
*C07D 309/04* (2006.01)
*C07D 309/06* (2006.01)
*C07D 309/08* (2006.01)
*C09D 309/12* (2006.01)
*C09D 309/14* (2006.01)

(52) U.S. Cl. ............ 428/1.1; 252/299.61; 252/299.66; 549/416; 549/419; 549/420; 549/426; 549/427; 549/428

(58) Field of Classification Search ............... 428/1.1; 252/299.01, 299.61, 299.67; 549/416, 419, 549/420, 426, 427, 428
See application file for complete search history.

(56) References Cited

U.S. PATENT DOCUMENTS

| | | | |
|---|---|---|---|
| 4,818,431 A | | 4/1989 | Eidenschink et al. |
| 6,565,933 B2 * | | 5/2003 | Tarumi et al. ............... 428/1.1 |
| 6,596,350 B2 * | | 7/2003 | Tarumi et al. ............... 428/1.1 |
| 6,669,998 B2 * | | 12/2003 | Tarumi et al. ............... 428/1.1 |
| 6,685,996 B2 * | | 2/2004 | Tarumi et al. ............... 428/1.1 |
| 6,692,657 B1 | | 2/2004 | Kato et al. |
| 6,929,833 B2 * | | 8/2005 | Tarumi et al. ............... 428/1.1 |
| 7,189,440 B2 * | | 3/2007 | Manabe et al. ............... 428/1.3 |
| 7,291,367 B2 * | | 11/2007 | Kirsch et al. ............... 428/1.1 |
| 2002/0060311 A1 * | | 5/2002 | Tarumi et al. ......... 252/299.66 |
| 2003/0203129 A1 | | 10/2003 | Tarumi et al. |

FOREIGN PATENT DOCUMENTS

| | | |
|---|---|---|
| DE | 41 32 006 A | 4/1993 |
| DE | 199 19 348 A | 11/1999 |
| DE | 103 53 658 A | 6/2004 |
| EP | 0 117 476 A | 9/1984 |
| EP | 0 969 071 A | 1/2000 |
| WO | WO 98/03610 A | 1/1998 |

\* cited by examiner

*Primary Examiner*—Shean C Wu
(74) *Attorney, Agent, or Firm*—Millen, White, Zelano, Branigan, P.C.

(57) ABSTRACT

The invention relates to liquid-crystalline compounds of formula (I), wherein $R^{11}$, $X^{11}$, $Z^{11}$, $Z^{12}$, $Z^{13}$, $L^{11}$, $L^{12}$, $L^{13}$, $L^{14}$, $L^{15}$ and $L^{16}$ have the meanings as cited in Claim 1, and to a method for the production thereof, their use in liquid-crystalline media, liquid-crystalline media containing at least one compound of formula (I), and to electro-optical displays containing a liquid-crystalline medium of this type

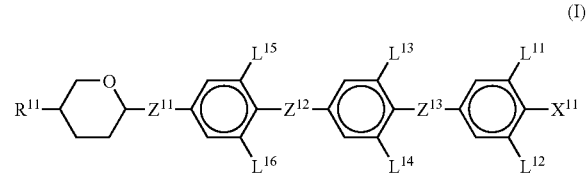

(I)

11 Claims, No Drawings

LIQUID-CRYSTALLINE COMPOUNDS HAVING A TETRAHYDROPYRAN RING

The present invention relates to liquid-crystalline compounds having a pyran ring and to a process for the preparation thereof, to a liquid-crystalline medium, to the use thereof for electro-optical purposes, and to displays containing this medium.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (superbirefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to meet various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, very high specific resistance, good UV and temperature stability and low vapour pressure are desired.

Matrix liquid-crystal displays of this type are known. Non-linear elements which can be used for individual switching of the individual pixels are, for example, active elements (i.e. transistors). The term "active matrix" is then used, where a distinction can be made between two types:
1. MOS (metal oxide semiconductor) or other diodes on a silicon wafer as substrate.
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are back-lit.

The term MLC displays here covers any matrix display with integrated non-linear elements, i.e., besides the active matrix, also displays with passive elements, such as varistors or diodes (MIM=metal-insulator-metal).

MLC displays of this type are particularly suitable for TV applications (for example pocket TVs) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. Furthermore, a high value of the voltage holding ratio (VHR, HR)—which represents a measure of the drop in the voltage applied to a display pixel over a time interval—is necessary for good image quality of an MLC display. The MLC displays from the prior art thus do not meet today's requirements.

Thus, there continues to be a great demand for MLC displays having very high specific resistance at the same time as a large working-temperature range, short response times even at low temperatures and low threshold voltage which do not have these disadvantages or only do so to a lesser extent.

In TN (Schadt-Helfrich) cells, media are desired which facilitate the following advantages in the cells:
  extended nematic phase range (in particular down to low temperatures)
  the ability to switch at extremely low temperatures (outdoor use, automobile, avionics)
  increased resistance to UV radiation (longer life)
  high $\Delta n$ for faster response times or smaller layer thicknesses of the displays
  high $\Delta \epsilon$ for a low threshold voltage $V_{th}$ The media available from the prior art do not allow these advantages to be achieved while simultaneously retaining the other parameters.

In the case of supertwisted (STN) cells, media are desired which facilitate greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

The invention is based on the object of providing media, in particular for MLC, IPS, TN or STN displays, which have improved properties or do not have the above-mentioned disadvantages or do so to a lesser extent, and preferably have high values of the dielectric anisotropy and optical anisotropy. This object requires mesogenic compounds having corresponding properties.

It has now been found that this object is achieved by the liquid-crystalline compounds according to the invention.

The invention thus relates to liquid-crystalline compounds of the formula I

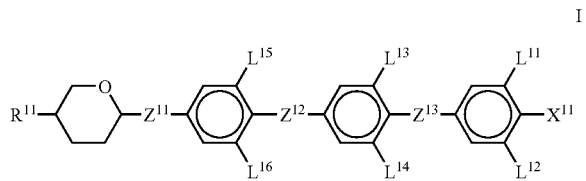

I where
$R^{11}$ denotes H, an alkyl or alkoxy radical having 1 to 15 carbon atoms or alkenyl or alkenyloxy radical having 2 to 15 carbon atoms, each of which is unsubstituted or mono- or polysubstituted by halogen, where, in addition, one or more $CH_2$ groups in these radicals may each, independently of one another, be replaced by —C≡C—, —CH=CH—, —O—, —CO—O— or —O—CO— in such a way that O atoms are not linked directly to one another;
$X^{11}$ denotes F, Cl, CN, NCS, $SF_5$, a halogenated alkyl radical, halogenated alkoxy radical, halogenated alkenyl radical or halogenated alkenyloxy radical, each having up to 7 C atoms, and
$Z^{11}$, $Z^{12}$
and $Z^{13}$ each, independently of one another, denote
—$C_2H_4$—, —C≡C—, —$C_2F_4$—, —CHO—, —OCH—, —COO—, —CF=CF—, —CH=CH—, —CH=CF—, —$CF_2O$—, —$OCF_2$—, —$(CH_2)_4$—, —$(CH_2)_3$— or a single bond,
$L^{11}$, $L^{12}$, $L^{13}$
$L^{14}$, $L^{15}$
and $L^{16}$, independently of one another, denote H or F.

The invention furthermore relates to the use of the compounds of the formula I in liquid-crystalline media. The invention furthermore relates to a liquid-crystalline medium having at least two liquid-crystalline compounds which is characterised in that it comprises at least one compound of the formula I according to the invention.

The compounds of the formula I have a broad range of applications. Depending on the choice of the substituents, these compounds can serve as base materials of which liquid-crystalline media are predominantly composed; however, it is also possible to add compounds of the formula I to liquid-crystalline base materials from other classes of compound in order, for example, to influence the dielectric and/or optical anisotropy of a dielectric of this type and/or to optimise its threshold voltage and/or its viscosity and/or its clearing point.

In the pure state, the compounds of the formula I are colourless and are suitable for the formation of liquid-crystalline mesophases in a temperature range which is favourably located for electro-optical use. The compounds according to the invention are distinguished by a high clearing point, high values of the dielectric and optical anisotropy and their broad nematic phase range. They result in a significant improvement in the low-temperature storage stability. They are stable chemically, thermally and to light.

Preferred compounds of the present invention are those in which the two substituents $L^{14}$ and $L^{16}$ both denote H.

Particularly preferred compounds according to the invention are those in which at least one of the two substituents $L^{13}$ and $L^{15}$ denotes F, i.e. at least one of the phenylene rings arranged between the terminal pyran ring and the terminal phenyl ring carries a fluorine substituent which is oriented in the direction of the terminal phenyl ring. $L^{13}$ very particularly preferably stands for fluorine.

It is furthermore preferred that at least one of the substituents $L^{11}$ and $L^{12}$ in the compounds of the formula I according to the invention stands for fluorine. $L^{11}$ and $L^{12}$ are particularly preferably simultaneously F.

It is furthermore preferred that $R^{11}$ in the compounds of the formula I according to the invention represents a straight-chain alkyl or alkenyl radical, in particular a straight-chain and unsubstituted alkyl or alkenyl radical having up to 1 or 2, 3, 4, 5, 6 or 7 carbon atoms respectively. Illustrative preferred radicals $R^{11}$ are, inter alia, methyl, ethyl, n-propyl, n-butyl, n-pentyl, n-hexyl, n-heptyl, vinyl, 1E-propenyl, 2-propenyl, 1E-butenyl, 3-butenyl, 1E-pentenyl, 3E-pentenyl, 1E-hexenyl and 1E-heptenyl.

$X^{11}$ preferably denotes F, Cl, CN, $CF_3$, $CF_2H$, $OCF_3$, $OCF_2H$, $OCFHCF_3$, $OCFHCH_2F$, $OCFHCH_2HF$, $OCF_2CH_3$, $OCF_2CH_2F$, $OCF_2CHF_2$, $OCF_2CF_2CF_2H$, $OCF_2CF_2CH_2F$, $OCFHCF_2CF_3$, $OCFHCF_2CHF_2$, $OCFHCFHCF_3$, $OCH_2CF_2CF_3$, $OCF_2CF_2CF_3$, $OCF_2CFHCHF_2$, $OCF_2CH_2CHF_2$, $OCFHCF_2CHF_2$, $OCFHCFHCHF_2$, $OCFHCH_2CF_3$, $OCH_2CFHCF_3$, $OCH_2CF_2CHF_2$, $OCF_2CFHCH_3$, $OCF_2CH_2CHF_2$, $OCFHCF_2CH_3$, $OCFHCFHCHF_2$, $OCFHCH_2CF_3$, $OCH_2CF_2CHF_2$, $OCH_2CFHCHF_2$, $OCF_2CH_2CH_3$, $OCFHCFHCH_3$, $OCFHCH_2CHF_2$, $OCH_2CF_2CH_3$, $OCH_2CFHCHF_2$, $OCH_2CH_2CHF_2$, $OCHCH_2CH_3$, $OCH_2CFHCH_3$, $OCH_2CH_2CHF_2$, $OCClFCF_3$, $OCClFCClF_2$, $OCClFCHF_2$, $OCFHCCl_2F$, $OCClFCHF_2$, $OCClFCClF_2$, $OCF_2CHCl_2$, $OCF_2CHCl_2$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CHF_2$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCHF_2$, $OCF_2CF_2CCl_2F$, $OCF_2CCl_2CHF_2$, $OCF_2CH_2CClF_2$, $OCClFCF_2CFH_2$, $OCFHCF_2CCl_2F$, $OCClFCFHCHF_2$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCHF_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, CH=$CF_2$, OCH=$CF_2$, CF=$CF_2$, OCF=$CF_2$, CF=CHF, OCF=CHF, CH=CHF, OCH=CHF in particular F, Cl, CN, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CHF$_2$.

It is furthermore preferred that $X^{11}$ in the compounds of the formula I according to the invention denotes F, Cl, CF$_3$, OCF$_3$, OCHF$_2$ or CN. $X^{11}$ is particularly preferably F, OCF$_3$, OCHF$_2$ or CN, in particular F, OCF$_3$ or CN.

Preferred embodiments of compounds of the formula I according to the invention are selected from compounds of the formulae I1 to I27:

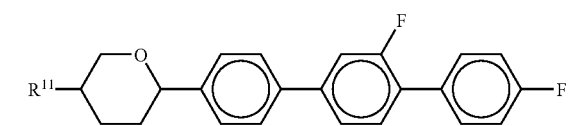

I1

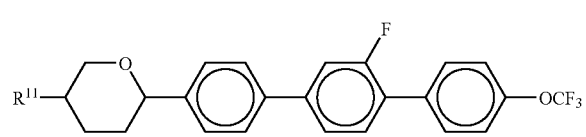

I2

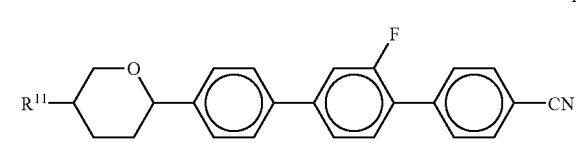

I3

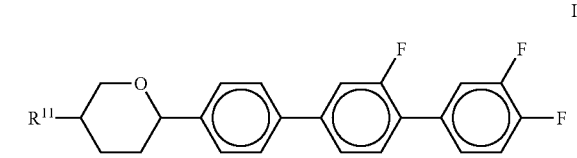

I4

I5

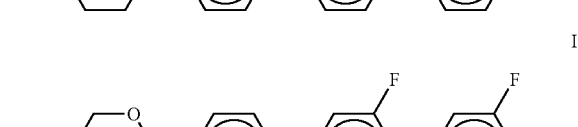

I6

I7

-continued

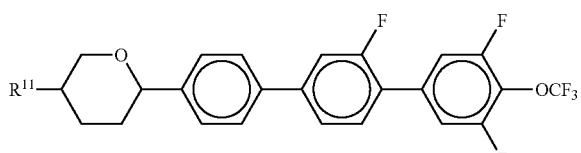

I8

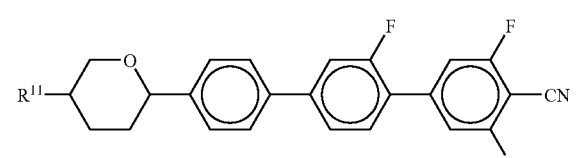

I9

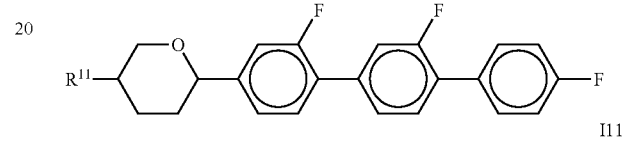

I10

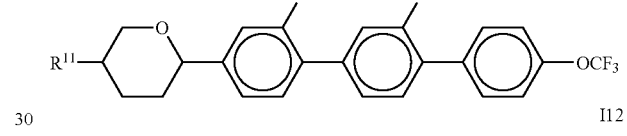

I11

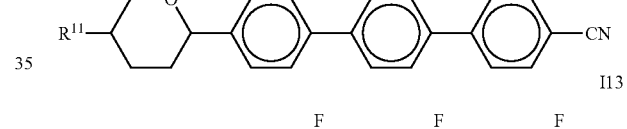

I12

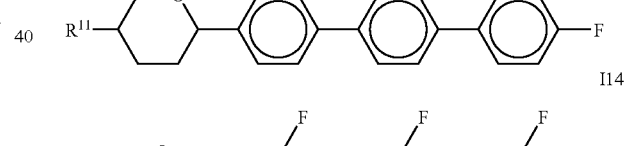

I13

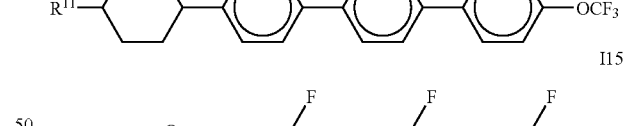

I14

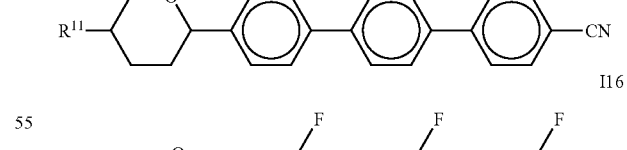

I15

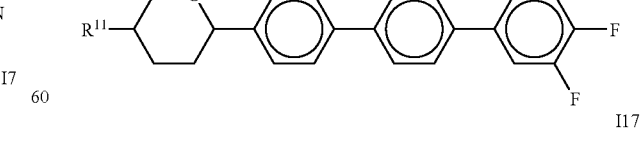

I16

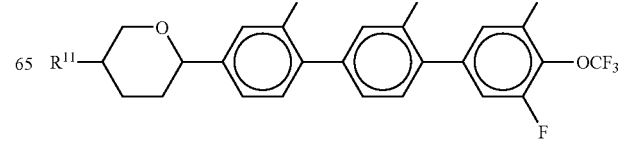

I17

-continued

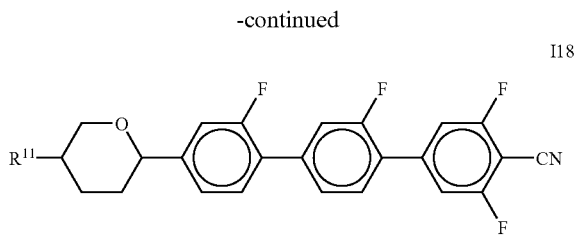
I18

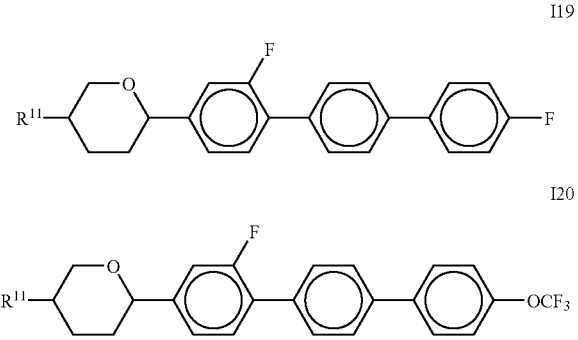
I19

I20

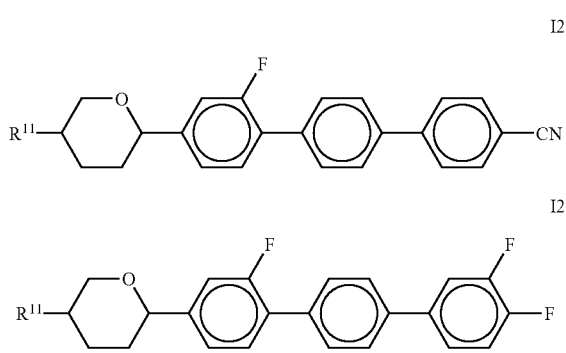
I21

I22

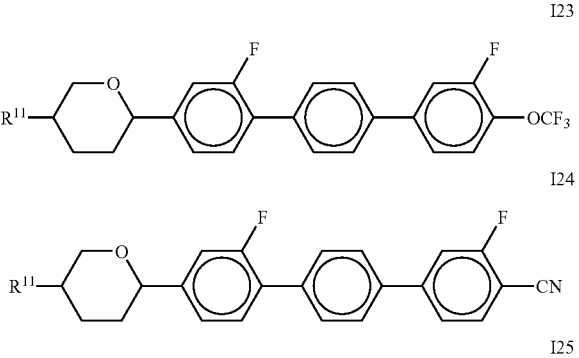
I23

I24

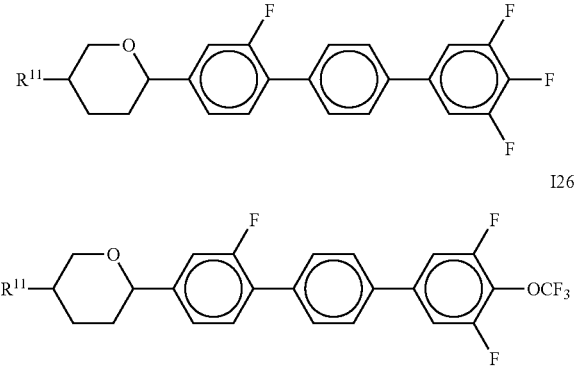
I25

I26

-continued

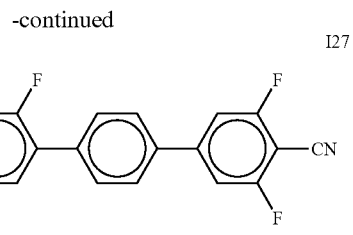
I27 where $R^{11}$ is as defined above for the formula I and preferably represents a straight-chain alkyl or alkenyl radical, in particular a straight-chain and unsubstituted alkyl or alkenyl radical having up to 1 or 2, 3, 4, 5, 6 or 7 carbon atoms respectively. Particularly preferred compounds are the compounds of the formulae I1 to I18, in particular of the formulae I1 to I9.

The present invention furthermore relates to a process for the preparation of the compounds of the formula I according to the invention which is characterised in that a compound of the formula AI is reacted with a compound of the formula BI in the presence of a palladium complex catalyst:

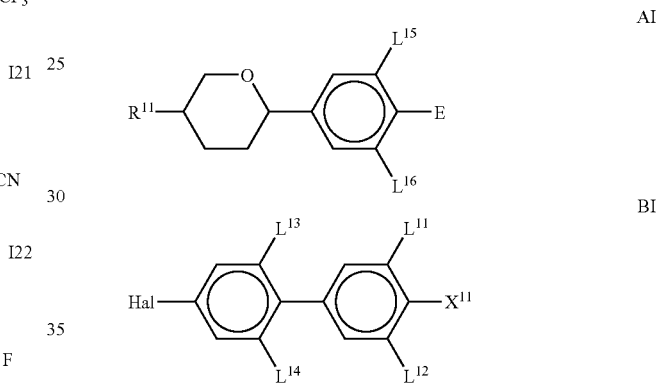

where
$R^{11}, X^{11}, L^{11}, L^{12}, L^{13}, L^{14}, L^{15}$ and $L^{16}$ are as defined above for the formula I,
Hal denotes chlorine, bromine or iodine, and
E denotes —B(OH)$_2$ or a boronate radical.
Hal is preferably bromine and E is preferably —B(OH)$_2$.

The palladium complex catalyst is preferably a Pd(0) catalyst, as is usually used for a transition metal-catalysed C—C coupling reaction of this type (cf. N. Miyaura, A. Suzuki, Chem. Rev. 1995, 95, 2457, and references cited therein). In particular, Pd(PPh$_3$)$_4$ is used as palladium complex catalyst. The amount of catalyst to be employed is generally between 20 and 0.1 mol %, preferably between 10 and 0.5 mol % and in particular between 5 and 1 mol %, in each case based on compound AI.

Boronate radicals are taken to mean, in particular, boronic acid ester radicals —B(OR$^x$)$_2$ or —B(OR$^y$O) (cf. N. Miyaura, A. Suzuki, Chem. Rev. 1995, 95, 2457, and references cited therein), where preferably R$^x$ stands for alkyl radicals and R$^y$ stands for an alkylene bridge and OR$^y$O bonds to the boron atom via both oxygen atoms.

The reaction according to the invention takes place under the usual conditions for transition metal-catalysed C—C coupling reactions of this type (cf. N. Miyaura, A. Suzuki, Chem. Rev. 1995, 95, 2457, and references cited therein). The two reactants AI and BI are reacted using a Pd(0) catalyst in a suitable solvent, such as, for example, toluene, and optionally in the presence of a pH buffer. The buffer system employed can be, for example, sodium borate buffer pH 9. The reaction temperature is room temperature to the boiling point of the solvent, preferably 40 to 100° C., in particular 70 to 90° C. The reaction time is not crucial per se and is selected so that the most complete reaction possible of the starting compounds AI and BI is achieved; it is generally between 1 h and 48 h, preferably 4 h and 24 h, in particular 8 h and 20 h.

The compounds of the formula AI and BI are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail. The compounds of the formula I according to the invention are also accessible correspondingly by processes other than the process according to the invention.

Scheme 1 shows a process for the preparation of the compounds of the formula I according to the invention via the compounds of the formula AI-1 and BI-1.

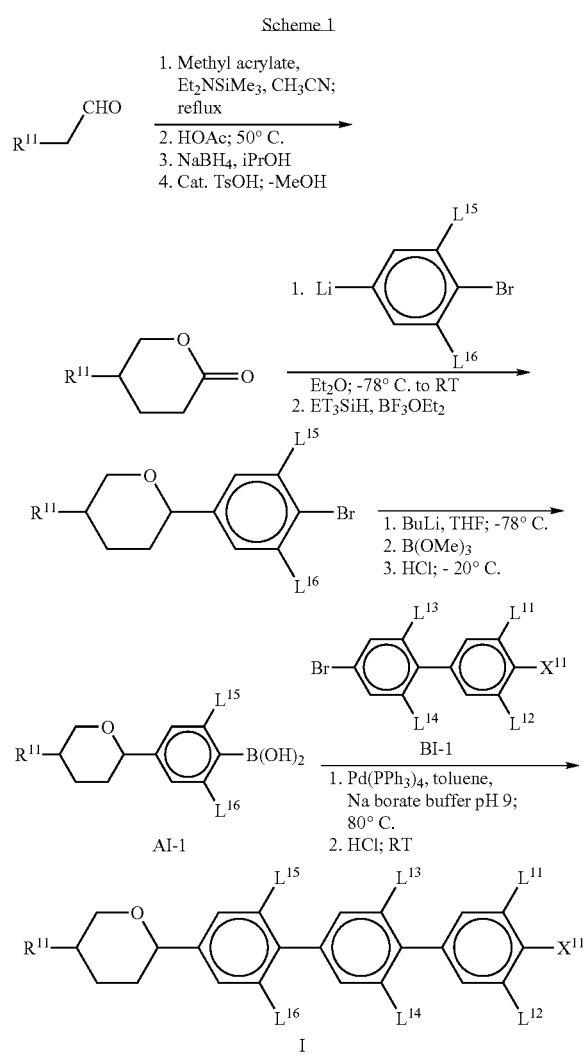

Scheme 2 shows a process for the preparation of the compounds of the formula BI-1.

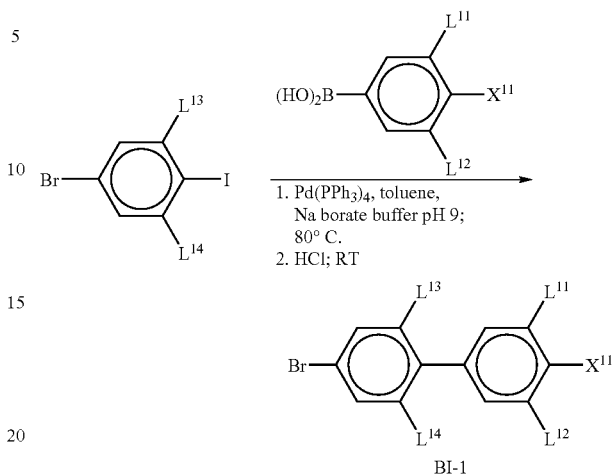

If radicals or substituents of the compounds according to the invention or the compounds according to the invention themselves can exist as optically active radicals, substituents or compounds since they have, for example, an asymmetric centre, these are also covered by the present invention. It goes without saying here that the compounds of the formula I according to the invention can exist in isomerically pure form, for example as pure enantiomers or diastereomers, or as a mixture of a plurality of isomers, for example as racemate.

If $R^{11}$ in the formula I does not denote H, the compounds of the formula I according to the invention can, owing to the disubstitution of the pyran ring, exist both as cis and also as trans isomers. In general, the respective trans isomer is preferred for many uses. It can be obtained selectively, inter alia, by employing in the preparation process a precursor having a pyran ring with the trans configuration, which is itself obtained, for example, by isomerisation using a base or acid or in particular by recrystallisation, fractional distillation and/or chromatographic separation. These conventional processes can naturally also be carried out with isomer mixtures of the compound of the formula I.

The liquid-crystalline media according to the invention comprise at least one compound of the formula I. They are preferably based on a plurality (preferably two, three or more) of compounds of the formula I, the proportion of these compounds is generally 2-95%, preferably 5-60% and particularly preferably in the range from 5-40%.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of the media according to the invention can be characterised by the formulae 1, 2, 3, 4 and 5:

R'-L-E-R"  1

R'-L-COO-E-R"  2

R'-L-OOC-E-R"  3

R'-L-CH$_2$CH$_2$-E-R"  4

R'-L-CF$_2$O-E-R"  5

In the formulae 1, 2, 3, 4 and 5, L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group Cyc, Phe and Pyr and simultaneously one or more components selected from the compounds of the formulae 1, 2, 3, 4 and 5 in which one of the radicals L and E is selected from the group Cyc, Phe and Pyr and the other radical is selected from the group -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group -Phe-Cyc-, -Cyc-Cyc-, -G-Phe- and -G-Cyc-.

R' and/or R" each, independently of one another, denote alkyl, alkenyl, alkoxy, oxaalkyl, alkenyloxy or alkanoyloxy having up to 8 C atoms, —F, —Cl, —CN, —NCS, —(O)$_i$CH$_{3-(k+l)}$F$_k$Cl$_l$, where i is 0 or 1 and k and l are 1, 2 or 3.

In a smaller sub-group of the compounds of the formulae 1, 2, 3, 4 and 5, R' and R" each, independently of one another, denote alkyl, alkenyl, alkoxy, oxaalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or oxaalkyl.

In another smaller sub-group of the compounds of the formulae 1, 2, 3, 4 and 5, which is known as group B, R" denotes —F, —Cl, —NCS or —(O)$_i$CH$_{3-(k+l)}$F$_k$Cl$_l$, where i is 0 or 1 and k and l are 1, 2 or 3; the compounds in which R" has this meaning are referred to by the sub-formulae 1b, 2b, 3b, 4b and 5b. Particular preference is given to those compounds of the sub-formulae 1b, 2b, 3b, 4b and 5b in which R" has the meaning —F, —Cl, —NCS, —CF$_3$, —OCHF$_2$ or —OCF$_3$.

In the compounds of the sub-formulae 1b, 2b, 3b, 4b and 5b, R' has the meaning indicated for the compounds of the sub-formulae 1a to 5a and is preferably alkyl, alkenyl, alkoxy or oxaalkyl.

In a further smaller sub-group of the compounds of the formulae 1, 2, 3, 4 and 5, R" denotes —CN; this sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meaning indicated for the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also common. All these substances are obtainable by methods which are known from the literature or analogously thereto.

Besides compounds of the formula I according to the invention, the media according to the invention preferably comprise one or more compounds selected from groups A and/or B and/or C. The proportions by weight of the compounds from these groups in the media according to the invention are preferably:

group A: 0 to 90%, preferably 20 to 90%, particularly preferably 30 to 90%;

group B: 0 to 80%, preferably 10 to 80%, particularly preferably 10 to 65%;

group C: 0 to 80%, preferably 5 to 80%, particularly preferably 5 to 50%;

where the sum of the proportions by weight of the group A and/or B and/or C compounds present in the respective media according to the invention is preferably 5 to 90% and particularly preferably 10 to 90%.

The liquid-crystal mixtures according to the invention enable a significant broadening of the available parameter latitude.

The achievable combinations of clearing point, thermal and UV stability and dielectric and optical anisotropy are far superior to previous materials from the prior art.

The requirement for a high clearing point, nematic phase at low temperature and a high $\Delta\epsilon$ has hitherto only been achieved to an inadequate extent. Known mesogenic compounds and liquid-crystal (LC) mixtures comprising them having a corresponding clearing point and comparable viscosity have lower $\Delta\epsilon$ values and thus a higher threshold voltage $V_{th}$. Although other known mesogenic compounds or the LC mixtures comprising them have similarly high $\Delta\epsilon$ values and low threshold voltage values, they are, however, significantly more viscous and/or have significantly lower clearing points.

The liquid-crystal mixtures according to the invention, while retaining the nematic phase down to −20° C. and preferably down to −30° C., particularly preferably down to −40° C., enable clearing points above 80°, preferably above 90°, particularly preferably above 100° C., simultaneously dielectric anisotropy values $\Delta\epsilon \geq 4$, preferably $\geq 6$, and a high value for the specific resistance to be achieved, enabling excellent STN and MLC displays to be obtained. In particular, the mixtures are characterised by low operating voltages. The TN thresholds are below 1.8 V, preferably below 1.6 V.

It goes without saying that, through a suitable choice of the components of the mixtures according to the invention, it is also possible for higher clearing points (for example above 110°) to be achieved at higher threshold voltages or lower clearing points to be achieved at lower threshold voltages with retention of the other advantageous properties. At viscosities correspondingly increased only slightly, it is likewise possible to obtain mixtures having greater $\Delta\epsilon$ and thus lower thresholds. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (DE 30 22 818 A1), a lower dielectric anisotropy is sufficient at the same threshold voltage as in an analogous display at the second minimum. This enables significantly higher specific resistance values to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The flow viscosity $\nu_{20}$ at 20° C. is preferably <60 mm$^2$·s$^{-1}$, particularly preferably <50 mm$^2$·s$^{-1}$. The nematic phase range is preferably at least 90°, in particular at least 100°. This range preferably extends at least from −30° to +80°. The rotational viscosity $\gamma_1$ at 20° C. is preferably <200 mPa·s, particularly preferably <180 mPa·s, in particular <160 mPa·s.

Measurements of the capacity holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR with increasing temperature than analogous mixtures comprising cyanophenylcyclohexanes of the formula

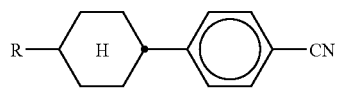

or esters of the formula

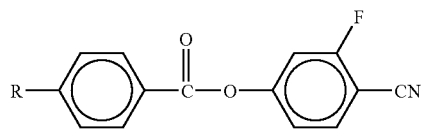

instead of the compounds of the formula I.

The UV stability of the mixtures according to the invention is also considerably better, i.e. they exhibit a significantly smaller decrease in the HR on exposure to UV.

The optimum mixing ratio of the compounds of the formula I and the compounds of groups A, B and C depends substantially on the desired properties, on the choice of the components of groups A, B and/or C and on the choice of any other components present. Suitable mixing ratios within the above-indicated range can easily be determined from case to case.

The liquid-crystal mixtures according to the invention are prepared in a manner conventional per se. In general, the desired amount of the components used in smaller amount is dissolved in the components making up the principal constituent, preferably at elevated temperature. It is also possible to mix solutions of the components in an organic solvent, for example in acetone, chloroform or methanol, and, after thorough mixing, to remove the solvent again, for example by distillation. It is furthermore possible to prepare the mixtures in other conventional ways, for example by using premixes, for example homologue mixtures, or using so-called "multi-bottle" systems.

The medium according to the invention may optionally comprise further additives known to the person skilled in the art and described in the literature, for example stabilisers, chiral dopants or dichroic dyes, in the usual concentrations. The total concentration of these further constituents is in the range from 0% to 15%, preferably in the range from 0.1% to 10% and is in particular not greater than 6%, based on the mixture as a whole. The concentrations of the individual compounds of these are generally in the range from 0.1% to 3%. The concentrations of these additives and similar constituents of the mixture are not taken into account when indicating the concentration ranges of the other mixture constituents.

The invention also relates to electro-optical displays (in particular STN or MLC displays having two plane-parallel outer plates, which, with a frame, form a cell, integrated non-linear elements for switching individual pixels on the outer plates, and a nematic liquid-crystal mixture of positive dielectric anisotropy and high specific resistance located in the cell) which contain media of this type, and to the use of these media for electro-optical purposes.

The construction of the MLC display according to the invention from polarisers, electrode base plates and electrodes having surface treatment corresponds to the usual design for displays of this type. The term usual design here is broadly drawn and also encompasses all derivatives and modifications of the MLC display, in particular also matrix display elements based on poly-Si TFTs or MIM.

An essential difference of the displays according to the invention from the displays conventional hitherto based on the twisted nematic cell consists, however, in the choice of the liquid-crystal parameters of the liquid-crystal layer.

In connection with the present invention, the term "alkyl"—unless defined otherwise elsewhere in this description or in the claims—denotes a straight-chain or branched aliphatic hydrocarbon radical having 1 to 15 (i.e. 1, 2, 3, 4, 5, 6, 7, 8, 9, 10, 11, 12, 13, 14 or 15) carbon atoms. If this alkyl radical is a saturated radical, it is also referred to as "alkanyl". One or more CH$_2$ groups in an alkyl radical may also be replaced by —O— ("oxaalkyl", "alkoxy"), —CH=CH— ("alkenyl"), —C≡C— ("alkynyl"), —CO—, —CO—O— or —O—CO— in such a way that oxygen atoms are not linked directly to one another. Alkyl is preferably a straight-chain radical having 1, 2, 3, 4, 5, 6 or 7 carbon atoms, in particular methyl, ethyl, n-propyl, n-butyl, n-pentyl, n-hexyl, n-heptyl. Groups having 2 to 5 carbon atoms are generally preferred. The alkyl radical may also be mono- or polysubstituted by halogen, in particular fluorine. CF$_3$ and CHF$_2$ are particularly preferred here.

Alkoxy is taken to mean an O-alkyl radical in which the oxygen atom is bonded directly to the group substituted by the alkoxy radical or to the substituted ring, and alkyl is as defined above and is preferably unbranched. Preferred alkoxy radicals are methoxy, ethoxy, propoxy, butoxy, pentoxy, hexoxy, heptoxy and octoxy. Alkoxy is particularly preferably —OCH$_3$, —OC$_2$H$_5$, —O-n-C$_3$H$_7$, —O-n-C$_4$H$_9$ and —O-n-C$_5$H$_{11}$. The alkoxy radical may also be mono- or polysubstituted by halogen, in particular fluorine. Particularly preferred fluorinated alkoxy radicals are OCF$_3$ and OCHF$_2$.

The term "alkenyl"—unless defined otherwise elsewhere in this description or in the claims—denotes an aliphatic hydrocarbon radical having at least one C=C double bond and encompasses in connection with the present invention straight-chain and branched alkenyl groups having 2 to 15 (i.e. 2, 3, 4, 5, 6, 7, 8, 9, 10, 11, 12, 13, 14 or 15) carbon atoms, in particular the straight-chain groups. The term "alkenyl" also encompasses radicals having 2 or more C=C double bonds. Preferred alkenyl groups are C$_2$-C$_7$-1E-alkenyl, C$_4$-C$_7$-3E-alkenyl, C$_5$-C$_7$-4-alkenyl, C$_6$-C$_7$-5-alkenyl, and C$_7$-6-alkenyl, in particular C$_2$-C$_7$-1E-alkenyl, C$_4$-C$_7$-3E-alkenyl and C$_5$-C$_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred. The alkenyl radical may also be mono- or polysubstituted by halogen, in particular fluorine. Particularly preferred fluorinated alkenyl radicals are CH=CHF, CF=CHF and CF=CF$_2$.

An "alkenyloxy" radical is taken to mean an O-alkenyl radical in which the oxygen atom is bonded directly to the group substituted by the alkenyloxy radical or to the substituted ring, and alkenyl is as defined above and is preferably unbranched. The alkenyloxy radical may also be mono- or polysubstituted by halogen, in particular fluorine. Particularly preferred fluorinated alkenyloxy radicals are OCH=CHF, OCF=CHF and OCF=CF$_2$.

Since one or more CH$_2$ groups in an alkyl radical may be replaced in accordance with the invention by —O—, the term "alkyl" also encompasses "oxaalkyl" radicals. In connection with the present invention, the term "oxaalkyl" denotes alkyl radicals in which at least one non-terminal CH$_2$ group has been replaced by —O— in such a way that there are no adjacent oxygen atoms. Oxaalkyl preferably encompasses straight-chain radicals of the formula —C$_a$H$_{2a+1}$—O—(CH$_2$)$_b$—, where a and b each, independently of one another, denote 1, 2, 3, 4, 5, 6, 7, 8, 9 or 10, with the proviso that a+b≦14. Particularly preferably, a is an integer from 1 to 6 and b is 1 or 2.

If one or more CH$_2$ groups in an alkyl radical or alkenyl radical have been replaced by —C≡C—, an alkynyl radical or alkenynyl radical is present. Replacement of one or more CH$_2$ groups by —CO—O— or —O—CO— is also possible. The corresponding radical may be straight-chain or branched. It is preferably straight-chain and has 2 to 6 carbon atoms. Accordingly, it particularly preferably denotes acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

If one CH$_2$ group in an alkyl radical has been replaced by unsubstituted or substituted —CH=CH— and an adjacent CH$_2$ group has been replaced by CO or —CO—O— or —O—CO—, this radical may be straight-chain or branched. It is preferably straight-chain and has 4 to 13 carbon atoms. Accordingly, it particularly preferably denotes acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine and polysubstitution are not excluded. Fluoroalkyl particularly preferably stands for CF$_3$. The term "fluoroalkoxy" correspondingly stands for an O-fluoroalkyl radical. Fluoroalkoxy particularly preferably stands for OCF$_3$ and OCHF$_2$.

The term "halogen" stands for fluorine, chlorine, bromine or iodine, while a "halogenated" radical is taken to mean a radical which is mono- or polysubstituted by fluorine, chlorine, bromine and/or iodine, in particular by fluorine.

C denotes a crystalline phase, S a smectic phase, S$_C$ a smectic C phase, S$_B$ a smectic B phase, S$_A$ a smectic A phase, N a nematic phase and I the isotropic phase.

V$_{10}$ denotes the voltage for 10% transmission (viewing angle perpendicular to the plate surface). t$_{on}$ denotes the switch-on time and t$_{off}$ the switch-off time at an operating voltage corresponding to twice the value of V$_{10}$. Δn denotes the optical anisotropy and n$_o$ or n$_e$ the refractive index. Δε denotes the dielectric anisotropy (Δε=ε$_∥$−ε$_⊥$, where ε$_∥$ denotes the dielectric constant parallel to the longitudinal axes of the molecules and ε$_⊥$ denotes the dielectric constant perpendicular thereto). The electro-optical data were measured in a TN cell at the 1st minimum (i.e. at a d·Δn value of 0.5) at 20° C., unless expressly stated otherwise. The optical data were measured at 20° C., unless expressly stated otherwise. γ$_1$ denotes the rotational viscosity in mPa·s at 20° C.

For the experimental determination of the physical parameters, the procedure as described in "Licristal, Physical Properties Of Liquid Crystals, Description of the measurement methods", ed. W. Becker, Merck KGaA, Darmstadt, revised edition, 1998, was carried out, where the properties of individual compounds were partly determined after measurement of a defined amount of the compound (usually 5 or 10% by weight) in a defined host mixture having known properties followed by extrapolation.

In the present application and in the following examples, the structures of the liquid-crystal compounds are indicated by means of acronyms, with the transformation into chemical formulae taking place in accordance with Tables A and B below. All radicals C$_n$H$_{2n+1}$ and C$_m$H$_{2m+1}$ are straight-chain alkyl radicals having n and m C atoms respectively. n and m each, independently of one another, 1 denote, 2, 3, 4, 5, 6, 7, 8, 9, 10, 11, 12, 13, 14 or 15. The coding in Table B is self-evident. In Table A, only the acronym for the parent structure is indicated. In individual cases this is followed, separated from the acronym for the parent structure by a dash, by a code for the substituents R$^1$, R$^2$, L$^1$ and L$^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |

-continued

| Code for $R^1$, $R^2$, $L^1$, $L^2$ | $R^1$ | $R^2$ | $L^1$ | $L^2$ |
|---|---|---|---|---|
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |

Preferred mixture components are shown in Tables A and B.

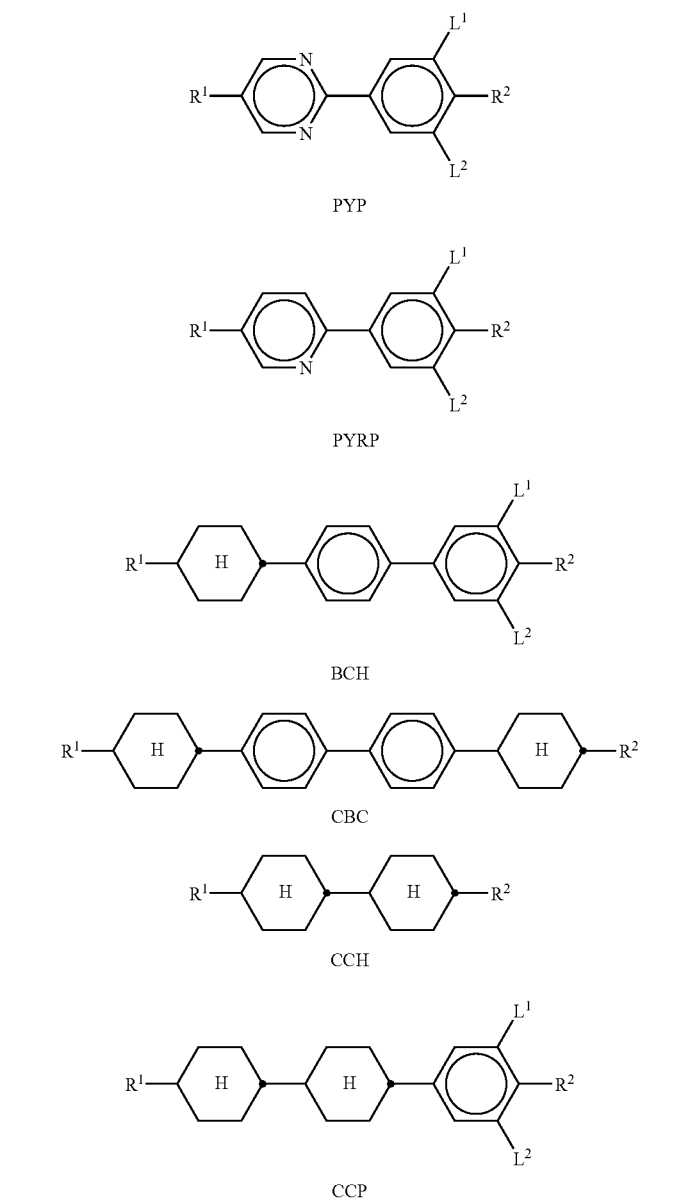

TABLE A

PYP

PYRP

BCH

CBC

CCH

CCP

TABLE A-continued
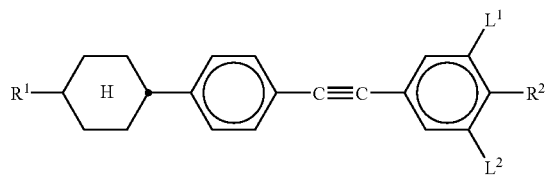
CPTP
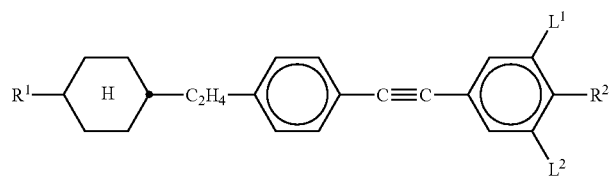
CEPTP
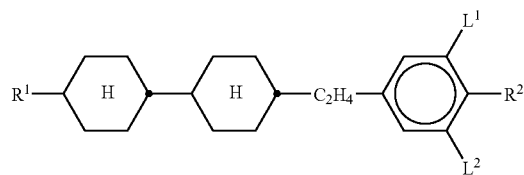
ECCP
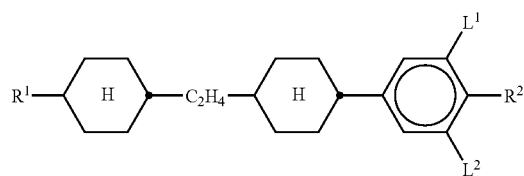
CECP
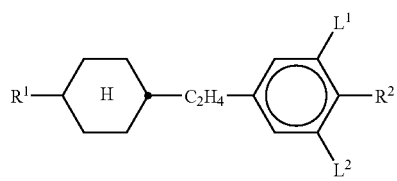
EPCH
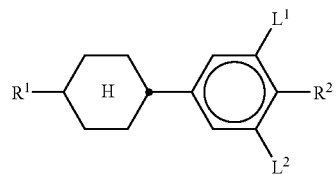
PCH
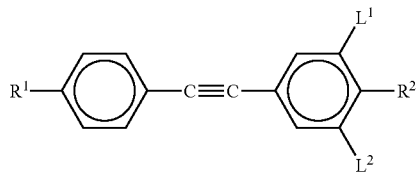
PTP TABLE A-continued
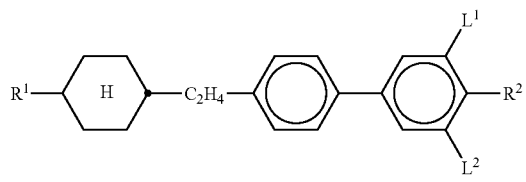
BECH
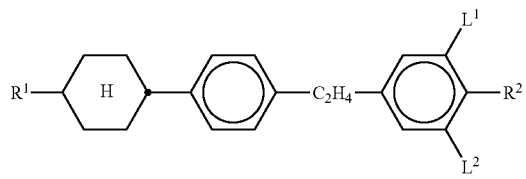
EBCH
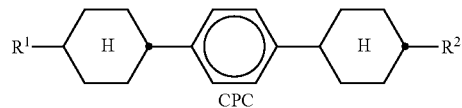
CPC
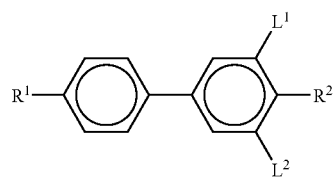
B
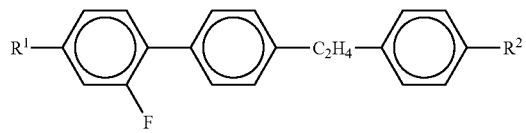
FET-nF
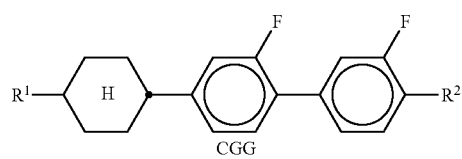
CGG
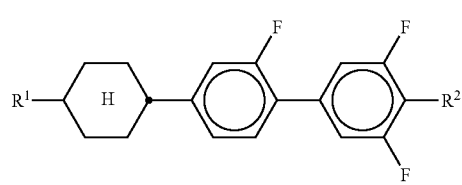
CGU
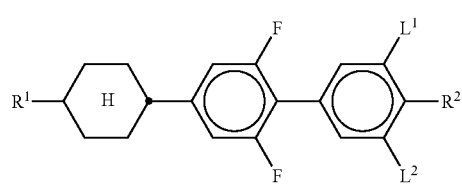
CUP TABLE A-continued
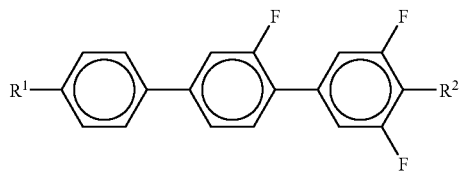
PGU
TABLE B
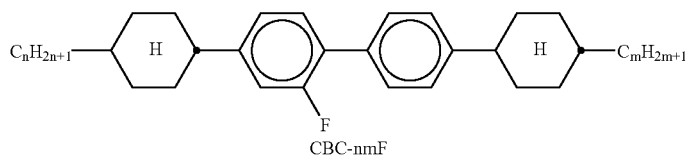
CBC-nmF
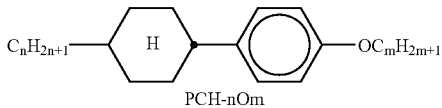
PCH-nOm
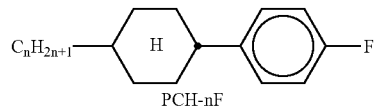
PCH-nF
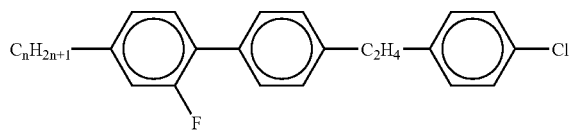
FET-nCl
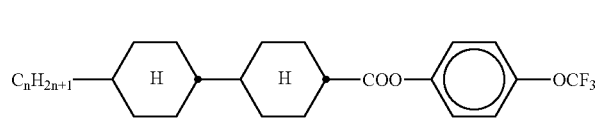
CP-nOCF$_3$
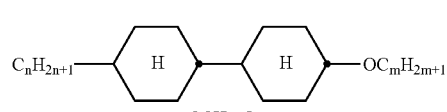
CCH-nOm
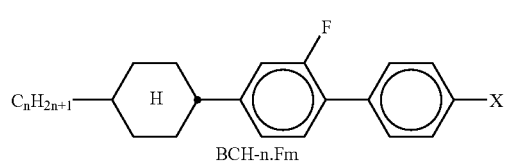
BCH-n.Fm
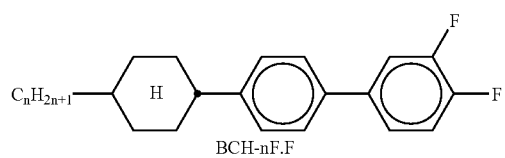
BCH-nF.F TABLE B-continued
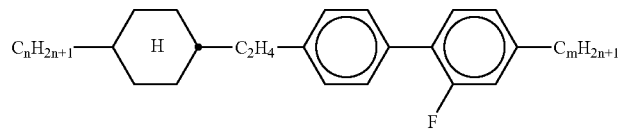
Inm
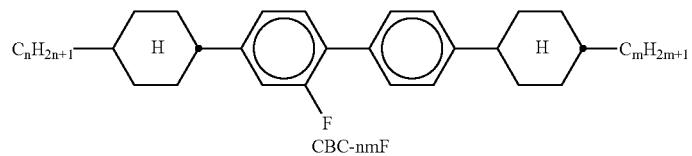
CBC-nmF
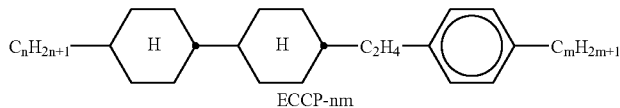
ECCP-nm
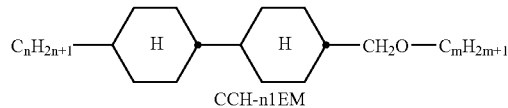
CCH-n1EM
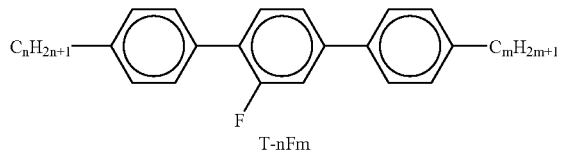
T-nFm
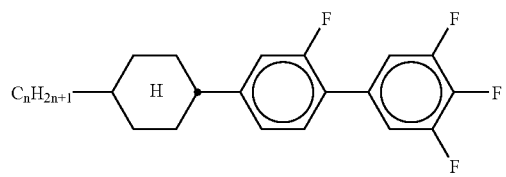
CGU-n-F
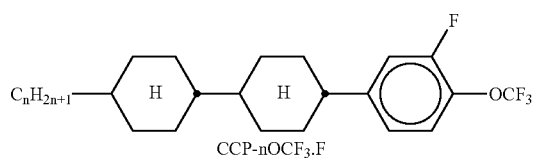
CCP-nOCF$_3$.F
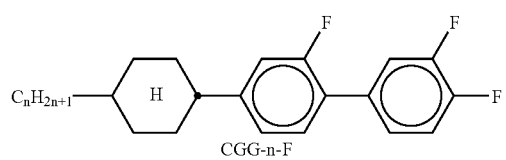
CGG-n-F
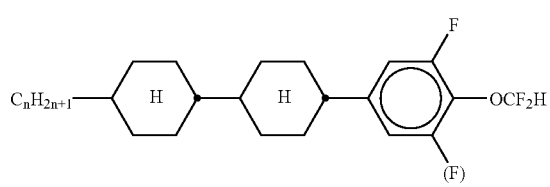
CCP-nOCF$_2$.F(.F)

TABLE B-continued
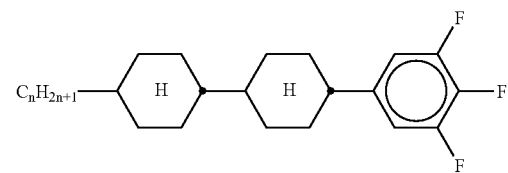
CCP-nF.F.F
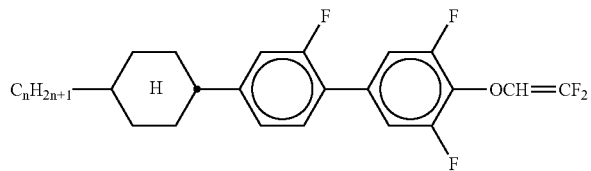
CGU-n-OXF
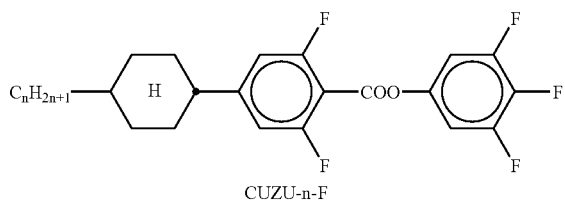
CUZU-n-F
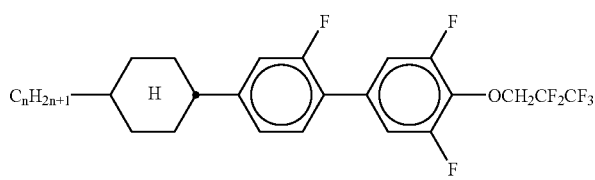
CGU-n-O1DT
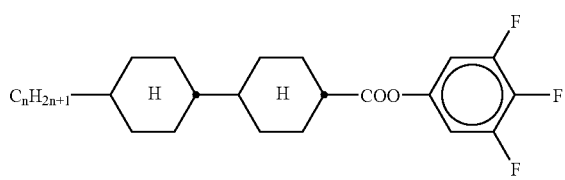
CCZU-n-F
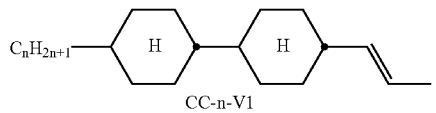
CC-n-V1
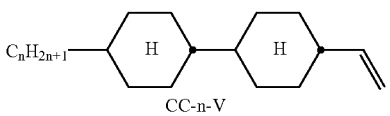
CC-n-V
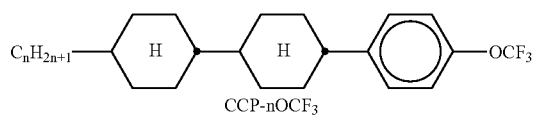
CCP-nOCF3

TABLE B-continued
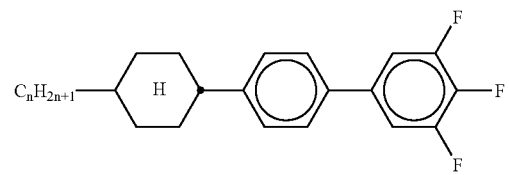
BCH-nF.F.F
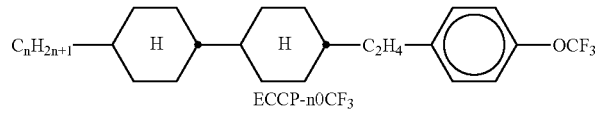
ECCP-nOCF₃
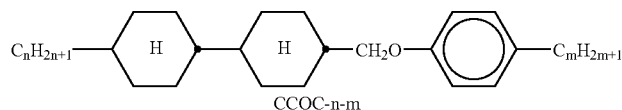
CCOC-n-m
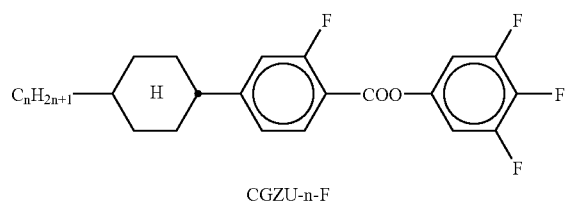
CGZU-n-F
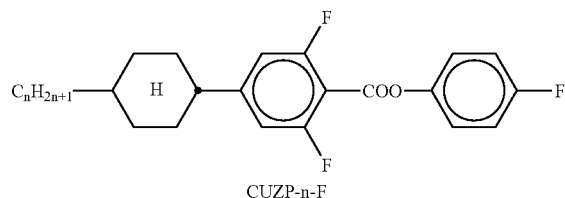
CUZP-n-F
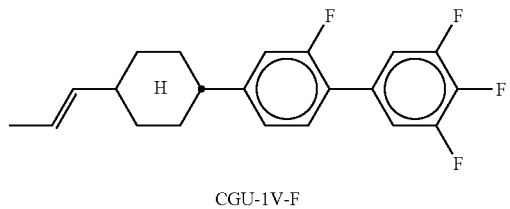
CGU-1V-F
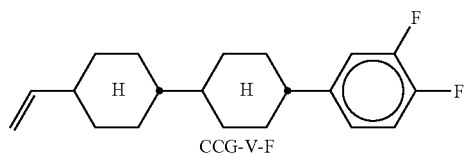
CCG-V-F
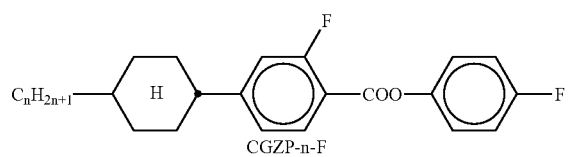
CGZP-n-F TABLE B-continued
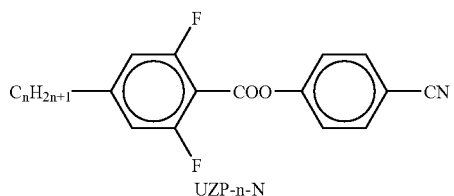
UZP-n-N
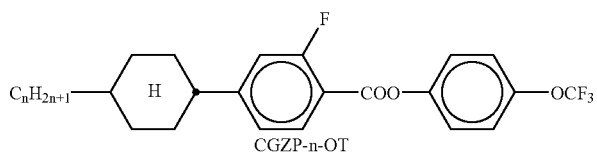
CGZP-n-OT
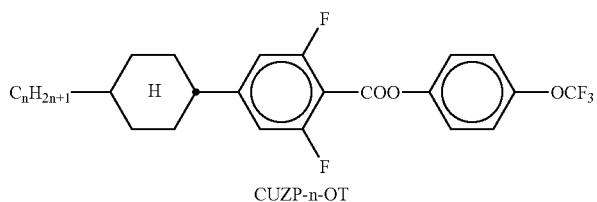
CUZP-n-OT
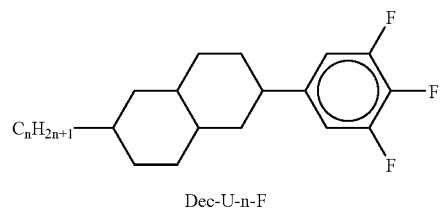
Dec-U-n-F
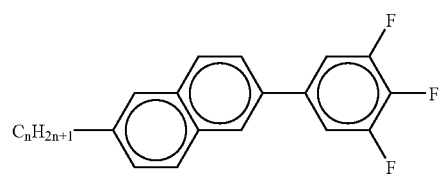
Nap-U-n-F
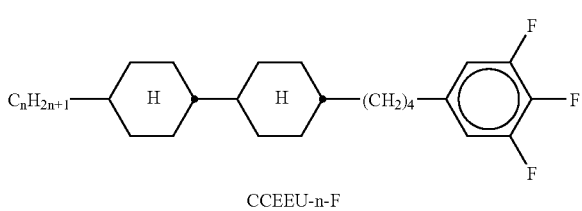
CCEEU-n-F
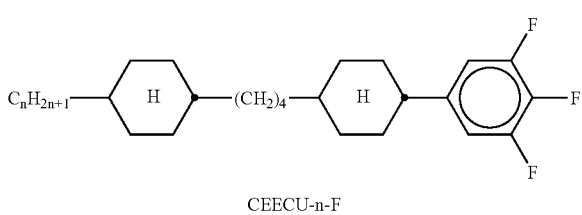
CEECU-n-F TABLE B-continued
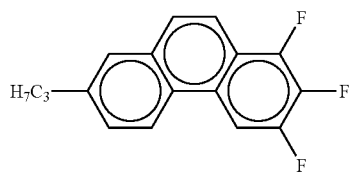
IS-9003
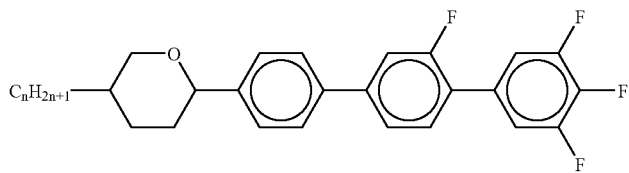
APGU-n-F
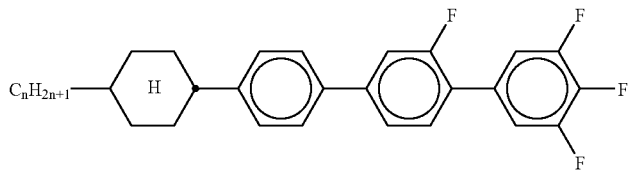
CPGU-n-F
TABLE C
Table C shows possible dopants which are generally added to the mixtures according to the invention in amounts of 0.05-10% by weight.
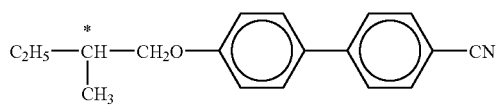
C 15
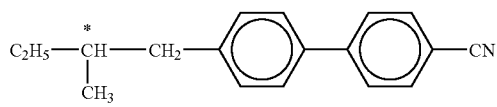
CB 15
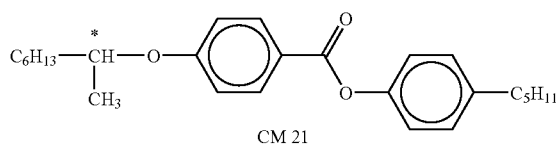
CM 21
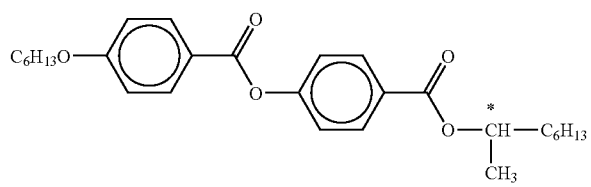
R/S-811

TABLE C-continued
Table C shows possible dopants which are generally added to the mixtures according to the invention in amounts of 0.05-10% by weight.
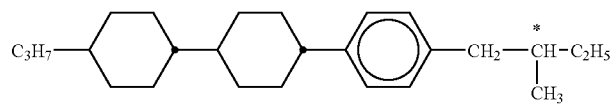
CM 44
CM45
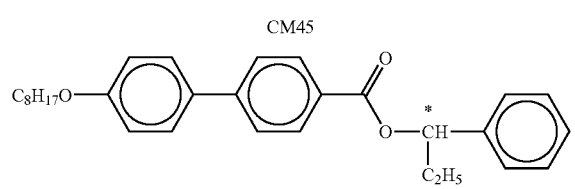
CM 47
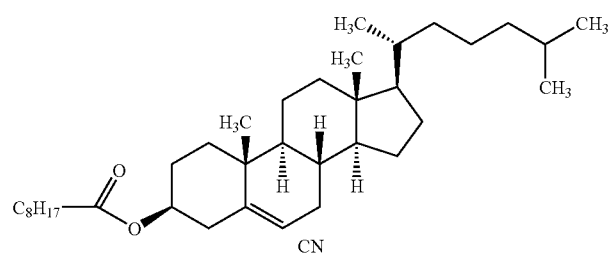
CN
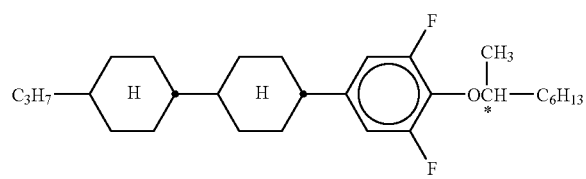
R/S-2011
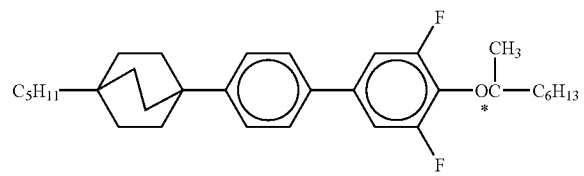
R/S-4011
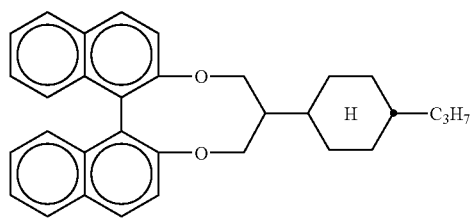
R/S-5011

TABLE D
Stabilisers which can be added, for example, to the mixtures according to the invention are mentioned below.
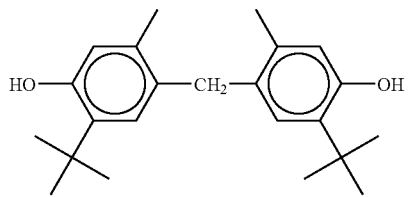
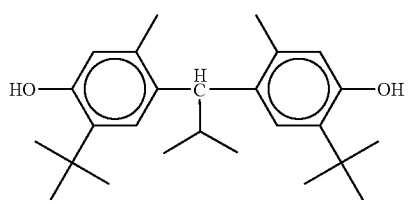
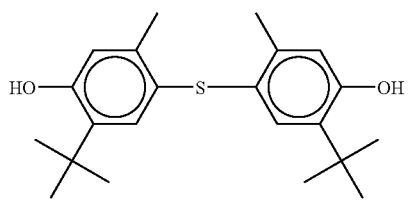
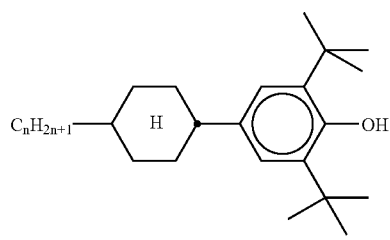
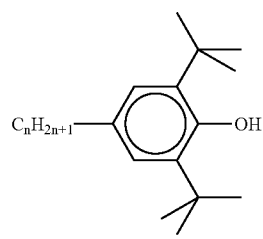
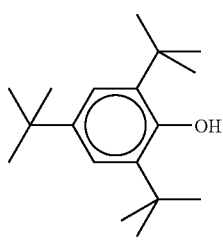

TABLE D-continued
Stabilisers which can be added, for example, to the mixtures according to the invention are mentioned below.
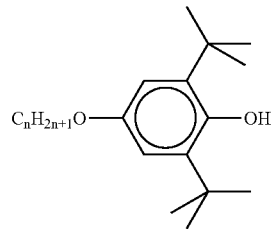
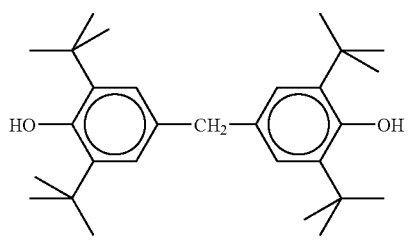
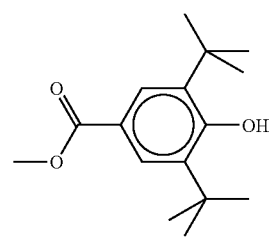
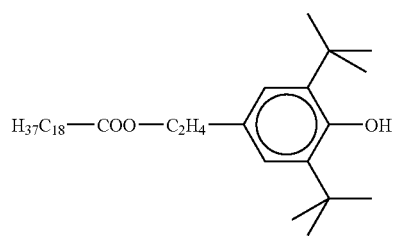
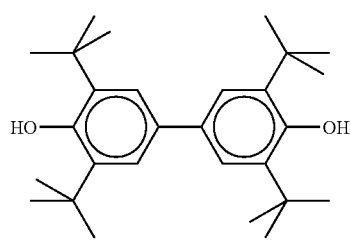

TABLE D-continued
Stabilisers which can be added, for example, to the mixtures according to the invention are mentioned below.
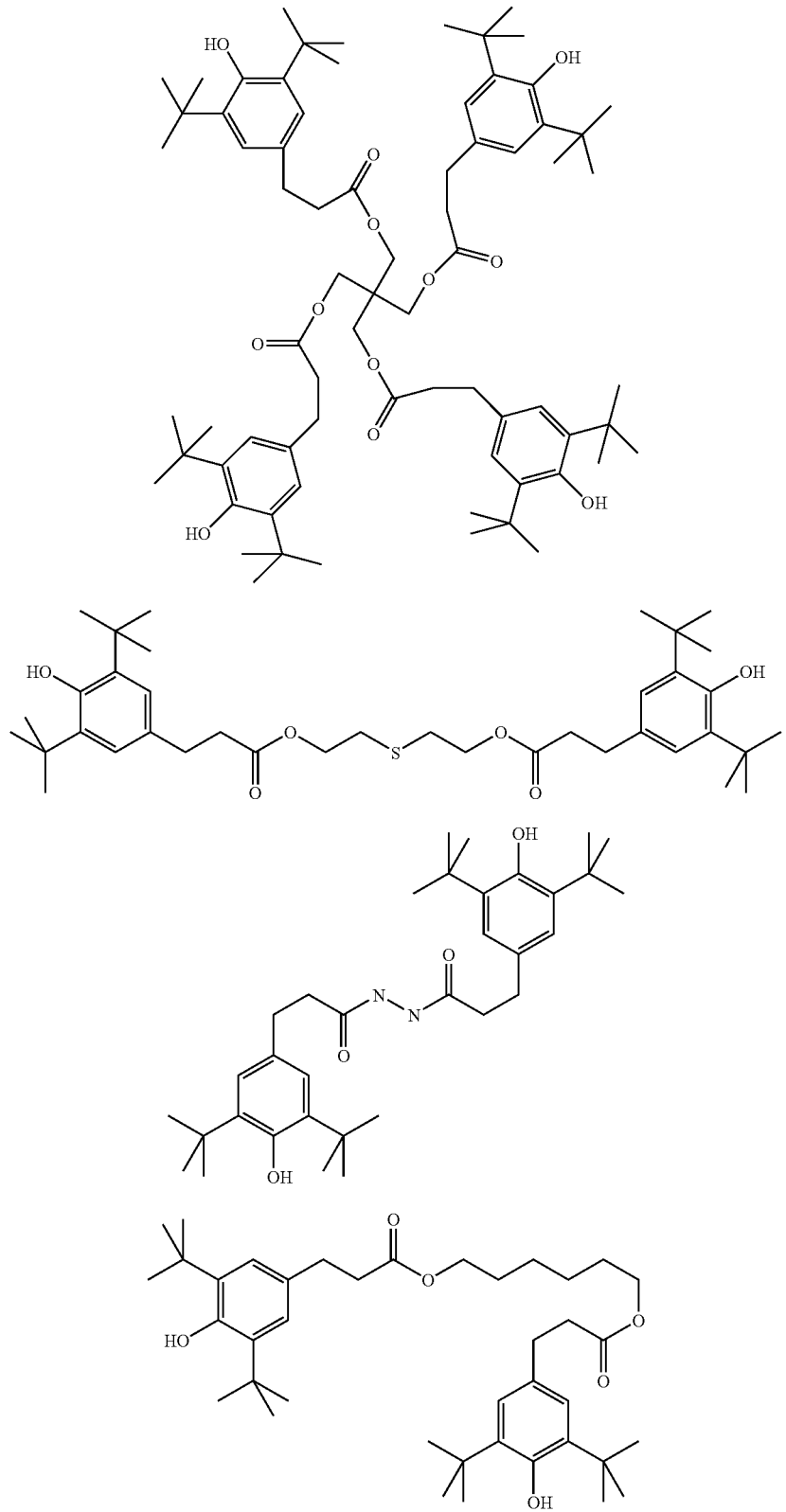

TABLE D-continued
Stabilisers which can be added, for example, to the mixtures according to the invention are mentioned below.
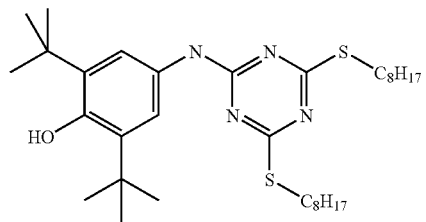
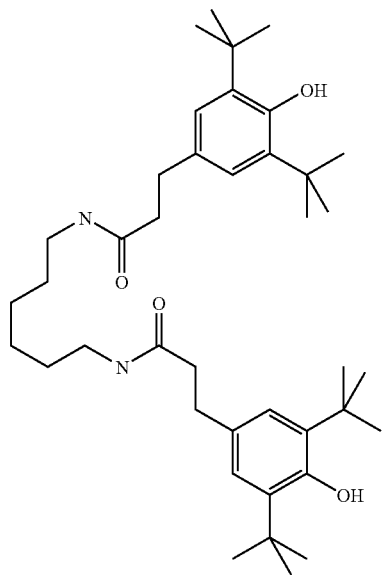
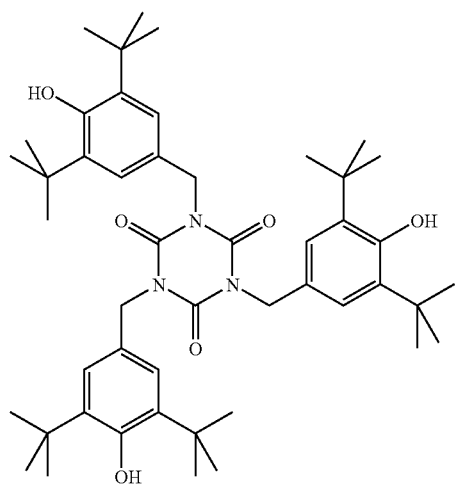

TABLE D-continued
Stabilisers which can be added, for example, to the mixtures according to the invention are mentioned below.
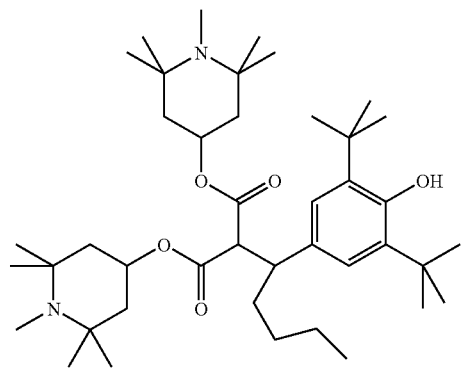
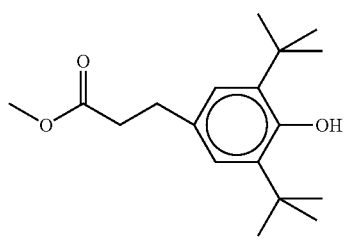
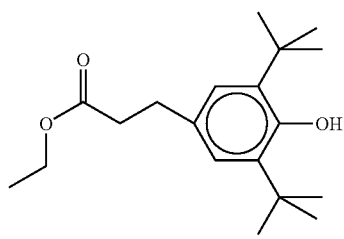
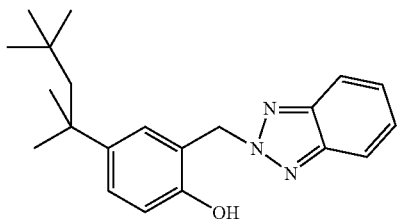
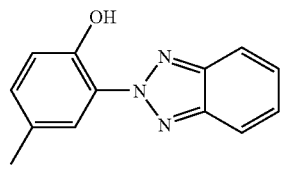
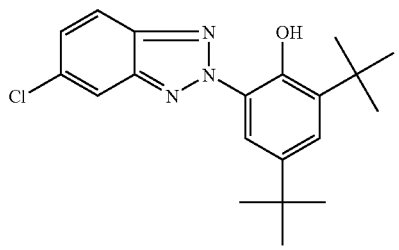

TABLE D-continued
Stabilisers which can be added, for example, to the mixtures according to the invention are mentioned below.
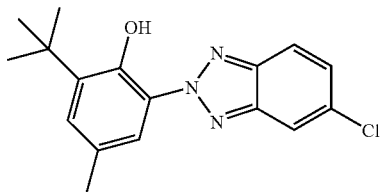
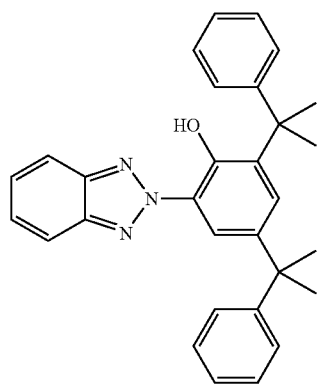
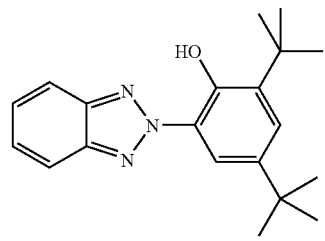
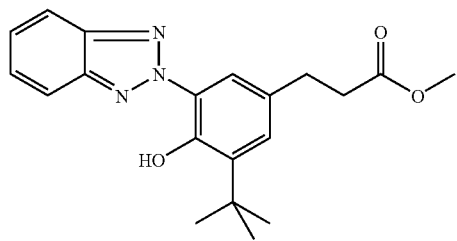
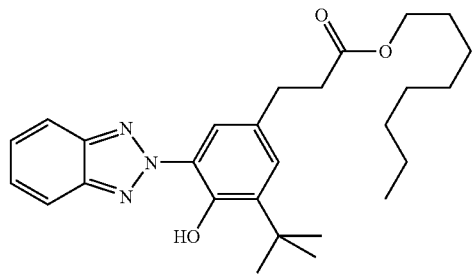

TABLE D-continued
Stabilisers which can be added, for example, to the mixtures according to the invention are mentioned below.
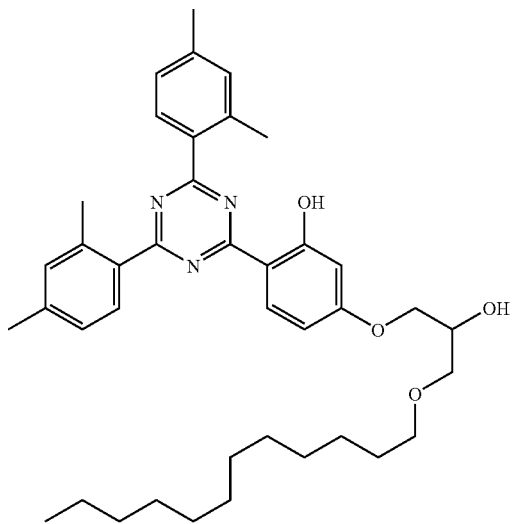
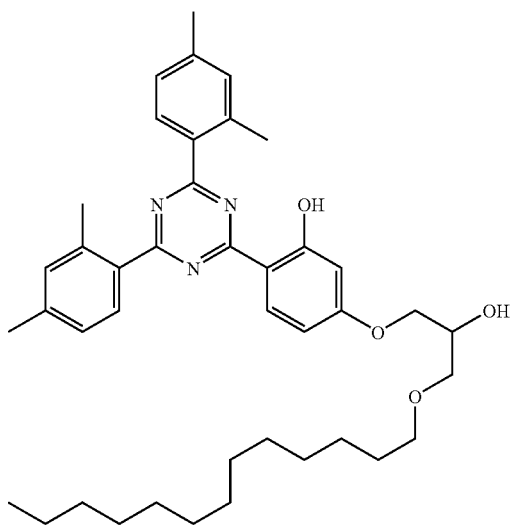
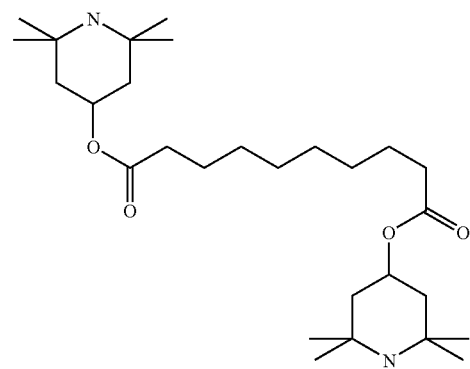

TABLE D-continued

Stabilisers which can be added, for example, to the mixtures according to the invention are mentioned below.

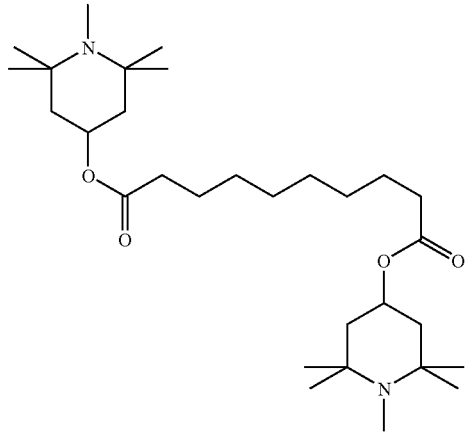

The following examples are intended to explain the invention without limiting it. Above and below, percentages denote percent by weight. All temperatures are indicated in degrees Celsius. m.p. denotes melting point, cl.p. denotes clearing point. Furthermore, C=crystalline state, N=nematic phase, S=smectic phase and I=isotropic phase. The data between these symbols represent the transition temperatures in ° C. Δn denotes optical anisotropy (589 nm, 20° C.), Δε the dielectric anisotropy 1 kHz, 20° C.), the flow viscosity $v_{20}$ (mm$^2$/sec) was determined at 20° C. The rotational viscosity $\gamma_1$ (mPa·s) was likewise determined at 20° C.

"Conventional work-up" means: water is added to the reaction mixture if necessary, the mixture is extracted with dichloromethane, diethyl ether, methyl tert-butyl ether or toluene, the phases are separated, the organic phase is dried and evaporated, and the product is purified by distillation under reduced pressure or crystallisation and/or chromatography. The following abbreviations are used in the examples and in the synthesis and reaction schemes:

| | |
|---|---|
| n-BuLi | 1.6 molar solution of n-butyllithium in n-hexane |
| DMAP | 4-(dimethylamino)pyridine |
| THF | tetrahydrofuran |
| DCC | N,N'-dicyclohexylcarbodiimide |
| LDA | lithium dimethylamide |
| Me | methyl |
| Et | ethyl |
| iPr | 2-propyl |
| Ph | phenyl |
| TsOH | toluenesulfonic acid |
| RT | room temperature |

EXAMPLE 1

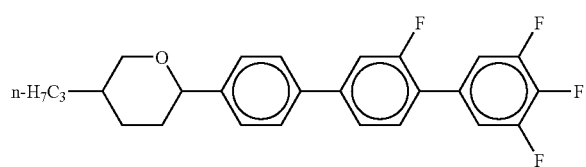

Step 1.1

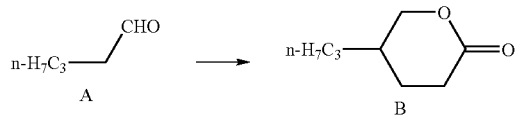

The preparation of B is carried out analogously to the lit. a) R. Baker, A. L. Boyes, C. J. Swain, *J. Chem. Soc. Perkin Trans.* 1, 1990, 1415-1421; b) H. Hagiwara, T. Okabe, H. Ono, V. P. Kamat. T. Hoshi, T. Suzuku, M. Ando, *J Chem. Soc. Perkin Trans.* 1, 2002, 895-900.

Step 1.2

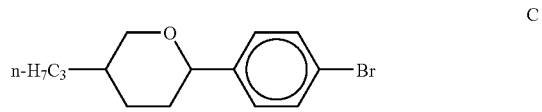

207 mmol of BuLi (15% in hexane) are added dropwise at −50° C. to a solution of 207 mmol of 1,4-dibromobenzene in 250 ml of diethyl ether. A solution of 170 mmol of B in 50 ml of diethyl ether is then added dropwise at the same temperature, the mixture is stirred for a further 30 min, allowed to come to 0° C. and subjected to conventional aqueous work-up. The crude product (51 g) is dissolved in 400 ml of CH$_2$Cl$_2$, and 400 mmol of triethylsilane are added at −75° C. 400 mmol of boron trifluoride etherate are added dropwise, during which the temperature must not rise above −70° C. The mixture is then allowed to come to −10° C., hydrolysed using sat. NaHCO$_3$ solution and subjected to conventional aqueous work-up. The crude product contains the trans/cis isomers in a ratio of 9:1. The product is recrystallised from pentane at −20° C.

Step 1.3

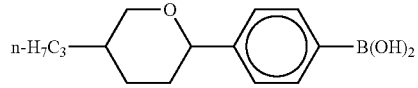

73 mmol of C are dissolved in 200 ml of THF and cooled to −70° C. Firstly 73 mmol of BuLi (15% in hexane) are added dropwise, followed by 73 mmol of trimethyl borate in 50 ml of THF. The mixture is allowed to come to −20° C., adjusted to pH=2 by addition of 2N HCl and subjected to aqueous work-up. The crude product is digested using hot heptane and crystallised at 0° C.

Step 1.4

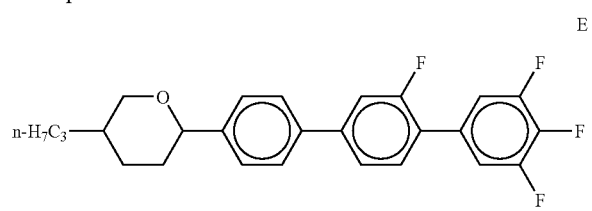

A mixture of 50 mmol of D, 50 mmol of 4-bromo-2,3', 4',5'-tetrafluorobiphenyl, 2.5 mmol of $Pd(PPh_3)_4$, 300 ml of toluene and 300 ml of Na borate buffer pH 9 is stirred at 80° C. for 18 h. The mixture is poured into 500 ml of 0.1N HCl, extracted with dichloromethane, dried over $Na_2SO_4$ and evaporated to dryness. The crude product is chromatographed in n-heptane on silica gel and then recrystallised twice from n-heptane. Colourless crystals. C 76 $S_A$ 132 N 207 I. $\Delta\epsilon=20.9^*$. $\Delta n=0.2243^*$. The known compound CPGU-3-F, which has a cyclohexane ring instead of the pyran ring, exhibits a significantly lower value for $\Delta\epsilon$ (17.2) while having comparable values for $\Delta n$ (0.2316).

(*: Determination of the parameters using a mixture of 10% by weight of the compound in the host mixture ZLI-4792 (Merck KGaA, Darmstadt) followed by extrapolation.)

The following compounds of the formula

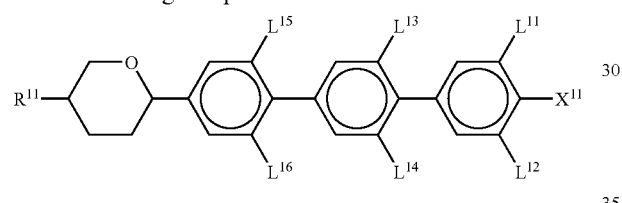

are prepared analogously to E (APGU-3-F; Example 1):

| Example | $R^{11}$ | $X^{11}$ | $L^{11}$ | $L^{12}$ | $L^{13}$ | $L^{14}$ | $L^{15}$ | $L^{16}$ |
|---|---|---|---|---|---|---|---|---|
| 2 | H | F | H | H | H | H | H | H |
| 3 | $CH_3$ | F | H | H | H | H | H | H |
| 4 | $C_2H_5$ | F | H | H | H | H | H | H |
| 5 | $n-C_3H_7$ | F | H | H | H | H | H | H |
| 6 | $n-C_4H_9$ | F | H | H | H | H | H | H |
| 7 | $n-C_5H_{11}$ | F | H | H | H | H | H | H |
| 8 | $n-C_6H_{13}$ | F | H | H | H | H | H | H |
| 9 | H | F | F | H | H | H | H | H |
| 10 | $CH_3$ | F | F | H | H | H | H | H |
| 11 | $C_2H_5$ | F | F | H | H | H | H | H |
| 12 | $n-C_3H_7$ | F | F | H | H | H | H | H |
| 13 | $n-C_4H_9$ | F | F | H | H | H | H | H |
| 14 | $n-C_5H_{11}$ | F | F | H | H | H | H | H |
| 15 | $n-C_6H_{13}$ | F | F | H | H | H | H | H |
| 16 | H | F | F | F | H | H | H | H |
| 17 | $CH_3$ | F | F | F | H | H | H | H |
| 18 | $C_2H_5$ | F | F | F | H | H | H | H |
| 19 | $n-C_3H_7$ | F | F | F | H | H | H | H |
| 20 | $nC_4H_9$ | F | F | F | H | H | H | H |
| 21 | $n-C_5H_{11}$ | F | F | F | H | H | H | H |
| 22 | $n-C_6H_{13}$ | F | F | F | H | H | H | H |
| 23 | H | F | F | F | F | H | H | H |
| 24 | $CH_3$ | F | F | F | F | H | H | H |
| 25 | $C_2H_5$ | F | F | F | F | H | H | H |
| 26 | $n-C_4H_9$ | F | F | F | F | H | H | H |
| 27 | $n-C_5H_{11}$ | F | F | F | F | H | H | H |
| 28 | $n-C_6H_{13}$ | F | F | F | F | H | H | H |
| 29 | H | F | F | F | F | F | H | H |
| 30 | $CH_3$ | F | F | F | F | F | H | H |
| 31 | $C_2H_5$ | F | F | F | F | F | H | H |
| 32 | $n-C_3H_7$ | F | F | F | F | F | H | H |
| 33 | $n-C_4H_9$ | F | F | F | F | F | H | H |
| 34 | $n-C_5H_{11}$ | F | F | F | F | F | H | H |
| 35 | $n-C_6H_{13}$ | F | F | F | F | F | H | H |
| 36 | H | F | F | F | F | F | F | H |
| 37 | $CH_3$ | F | F | F | F | F | F | H |
| 38 | $C_2H_5$ | F | F | F | F | F | F | H |
| 39 | $n-C_3H_7$ | F | F | F | F | F | F | H |
| 40 | $nC_4H_9$ | F | F | F | F | F | F | H |
| 41 | $n-C_5H_{11}$ | F | F | F | F | F | F | H |
| 42 | $n-C_6H_{13}$ | F | F | F | F | F | F | H |
| 43 | H | F | F | F | F | F | F | F |
| 44 | $CH_3$ | F | F | F | F | F | F | F |
| 45 | $C_2H_5$ | F | F | F | F | F | F | F |
| 46 | $n-C_3H_7$ | F | F | F | F | F | F | F |
| 47 | $nC_4H_9$ | F | F | F | F | F | F | F |
| 48 | $n-C_5H_{11}$ | F | F | F | F | F | F | F |
| 49 | $n-C_6H_{13}$ | F | F | F | F | F | F | F |
| 50 | H | F | F | F | F | H | F | H |
| 51 | $CH_3$ | F | F | F | F | H | F | H |
| 52 | $C_2H_5$ | F | F | F | F | H | F | H |
| 53 | $n-C_3H_7$ | F | F | F | F | H | F | H |
| 54 | $nC_4H_9$ | F | F | F | F | H | F | H |
| 55 | $n-C_5H_{11}$ | F | F | F | F | H | F | H |
| 56 | $n-C_6H_{13}$ | F | F | F | F | H | F | H |
| 57 | H | F | F | F | H | H | F | H |
| 58 | $CH_3$ | F | F | F | H | H | F | H |
| 59 | $C_2H_5$ | F | F | F | H | H | F | H |
| 60 | $n-C_3H_7$ | F | F | F | H | H | F | H |
| 61 | $nC_4H_9$ | F | F | F | H | H | F | H |
| 62 | $n-C_5H_{11}$ | F | F | F | H | H | F | H |
| 63 | $n-C_6H_{13}$ | F | F | F | H | H | F | H |
| 64 | H | F | F | H | F | H | F | H |
| 65 | $CH_3$ | F | F | H | F | H | H | H |
| 66 | $C_2H_5$ | F | F | H | F | H | H | H |
| 67 | $n-C_3H_7$ | F | F | H | F | H | H | H |
| 68 | $nC_4H_9$ | F | F | H | F | H | H | H |
| 69 | $n-C_5H_{11}$ | F | F | H | F | H | H | H |
| 70 | $n-C_6H_{13}$ | F | F | H | F | H | H | H |
| 71 | H | F | H | H | F | H | H | H |
| 72 | $CH_3$ | F | H | H | F | H | H | H |
| 73 | $C_2H_5$ | F | H | H | F | H | H | H |
| 74 | $n-C_3H_7$ | F | H | H | F | H | H | H |
| 75 | $nC_4H_9$ | F | H | H | F | H | H | H |
| 76 | $n-C_5H_{11}$ | F | H | H | F | H | H | H |
| 77 | $n-C_6H_{13}$ | F | H | H | F | H | H | H |
| 78 | H | F | F | H | F | H | F | H |
| 79 | $CH_3$ | F | F | H | F | H | F | H |
| 80 | $C_2H_5$ | F | F | H | F | H | F | H |
| 81 | $n-C_3H_7$ | F | F | H | F | H | F | H |
| 82 | $nC_4H_9$ | F | F | H | F | H | F | H |
| 83 | $n-C_5H_{11}$ | F | F | H | F | H | F | H |
| 84 | $n-C_6H_{13}$ | F | F | H | F | H | F | H |
| 85 | H | F | H | H | F | H | F | H |
| 86 | $CH_3$ | F | H | H | F | H | F | H |
| 87 | $C_2H_5$ | F | H | H | F | H | F | H |
| 88 | $n-C_3H_7$ | F | H | H | F | H | F | H |
| 89 | $nC_4H_9$ | F | H | H | F | H | F | H |
| 90 | $n-C_5H_{11}$ | F | H | H | F | H | F | H |
| 91 | $n-C_6H_{13}$ | F | H | H | F | H | F | H |
| 92 | H | Cl | H | H | H | H | H | H |
| 93 | $CH_3$ | Cl | H | H | H | H | H | H |
| 94 | $C_2H_5$ | Cl | H | H | H | H | H | H |
| 95 | $n-C_3H_7$ | Cl | H | H | H | H | H | H |
| 96 | $n-C_4H_9$ | Cl | H | H | H | H | H | H |
| 97 | $n-C_5H_{11}$ | Cl | H | H | H | H | H | H |
| 98 | $n-C_6H_{13}$ | Cl | H | H | H | H | H | H |
| 99 | H | Cl | F | H | H | H | H | H |
| 100 | $CH_3$ | Cl | F | H | H | H | H | H |
| 101 | $C_2H_5$ | Cl | F | H | H | H | H | H |
| 102 | $n-C_3H_7$ | Cl | F | H | H | H | H | H |
| 103 | $n-C_4H_9$ | Cl | F | H | H | H | H | H |
| 104 | $n-C_5H_{11}$ | Cl | F | H | H | H | H | H |
| 105 | $n-C_6H_{13}$ | Cl | F | H | H | H | H | H |
| 106 | H | Cl | F | F | H | H | H | H |
| 107 | $CH_3$ | Cl | F | F | H | H | H | H |
| 108 | $C_2H_5$ | Cl | F | F | H | H | H | H |
| 109 | $n-C_3H_7$ | Cl | F | F | H | H | H | H |
| 110 | $nC_4H_9$ | Cl | F | F | H | H | H | H |

-continued

| Example | $R^{11}$ | $X^{11}$ | $L^{11}$ | $L^{12}$ | $L^{13}$ | $L^{14}$ | $L^{15}$ | $L^{16}$ |
|---|---|---|---|---|---|---|---|---|
| 111 | n-C$_5$H$_{11}$ | Cl | F | F | H | H | H | H |
| 112 | n-C$_6$H$_{13}$ | Cl | F | F | H | H | H | H |
| 113 | H | Cl | F | F | F | H | H | H |
| 114 | CH$_3$ | Cl | F | F | F | H | H | H |
| 115 | C$_2$H$_5$ | Cl | F | F | F | H | H | H |
| 116 | n-C$_3$H$_7$ | Cl | F | F | F | H | H | H |
| 117 | nC$_4$H$_9$ | Cl | F | F | F | H | H | H |
| 118 | n-C$_5$H$_{11}$ | Cl | F | F | F | H | H | H |
| 119 | n-C$_6$H$_{13}$ | Cl | F | F | F | H | H | H |
| 120 | H | Cl | F | F | F | F | H | H |
| 121 | CH$_3$ | Cl | F | F | F | F | H | H |
| 122 | C$_2$H$_5$ | Cl | F | F | F | F | H | H |
| 123 | n-C$_3$H$_7$ | Cl | F | F | F | F | H | H |
| 124 | nC$_4$H$_9$ | Cl | F | F | F | F | H | H |
| 125 | n-C$_5$H$_{11}$ | Cl | F | F | F | F | H | H |
| 126 | n-C$_6$H$_{13}$ | Cl | F | F | F | F | H | H |
| 127 | H | Cl | F | F | F | F | F | H |
| 128 | CH$_3$ | Cl | F | F | F | F | F | H |
| 129 | C$_2$H$_5$ | Cl | F | F | F | F | F | H |
| 130 | n-C$_3$H$_7$ | Cl | F | F | F | F | F | H |
| 131 | nC$_4$H$_9$ | Cl | F | F | F | F | F | H |
| 132 | n-C$_5$H$_{11}$ | Cl | F | F | F | F | F | H |
| 133 | n-C$_6$H$_{13}$ | Cl | F | F | F | F | F | H |
| 134 | H | Cl | F | F | F | F | F | F |
| 135 | CH$_3$ | Cl | F | F | F | F | F | F |
| 136 | C$_2$H$_5$ | Cl | F | F | F | F | F | F |
| 137 | n-C$_3$H$_7$ | Cl | F | F | F | F | F | F |
| 138 | nC$_4$H$_9$ | Cl | F | F | F | F | F | F |
| 139 | n-C$_5$H$_{11}$ | Cl | F | F | F | F | F | F |
| 140 | n-C$_6$H$_{13}$ | Cl | F | F | F | F | F | F |
| 141 | H | Cl | F | F | F | H | F | H |
| 142 | CH$_3$ | Cl | F | F | F | H | F | H |
| 143 | C$_2$H$_5$ | Cl | F | F | F | H | F | H |
| 144 | n-C$_3$H$_7$ | Cl | F | F | F | H | F | H |
| 145 | nC$_4$H$_9$ | Cl | F | F | F | H | F | H |
| 146 | n-C$_5$H$_{11}$ | Cl | F | F | F | H | F | H |
| 147 | n-C$_6$H$_{13}$ | Cl | F | F | F | H | F | H |
| 148 | H | Cl | F | F | H | F | H | H |
| 149 | CH$_3$ | Cl | F | F | H | F | H | H |
| 150 | C$_2$H$_5$ | Cl | F | F | H | F | H | H |
| 151 | n-C$_3$H$_7$ | Cl | F | F | H | F | H | H |
| 152 | nC$_4$H$_9$ | Cl | F | F | H | F | H | H |
| 153 | n-C$_5$H$_{11}$ | Cl | F | F | H | F | H | H |
| 154 | n-C$_6$H$_{13}$ | Cl | F | F | H | F | H | H |
| 155 | H | Cl | F | H | F | H | H | H |
| 156 | CH$_3$ | Cl | F | H | F | H | H | H |
| 157 | C$_2$H$_5$ | Cl | F | H | F | H | H | H |
| 158 | n-C$_3$H$_7$ | Cl | F | H | F | H | H | H |
| 159 | nC$_4$H$_9$ | Cl | F | H | F | H | H | H |
| 160 | n-C$_5$H$_{11}$ | Cl | F | H | F | H | H | H |
| 161 | n-C$_6$H$_{13}$ | Cl | F | H | F | H | H | H |
| 162 | H | Cl | F | H | H | H | H | H |
| 163 | CH$_3$ | Cl | H | H | F | H | H | H |
| 164 | C$_2$H$_5$ | Cl | H | H | F | H | H | H |
| 165 | n-C$_3$H$_7$ | Cl | H | H | F | H | H | H |
| 166 | nC$_4$H$_9$ | Cl | H | H | F | H | H | H |
| 167 | n-C$_5$H$_{11}$ | Cl | H | H | F | H | H | H |
| 168 | n-C$_6$H$_{13}$ | Cl | H | H | F | H | H | H |
| 169 | H | Cl | F | H | F | H | F | H |
| 170 | CH$_3$ | Cl | F | H | F | H | F | H |
| 171 | C$_2$H$_5$ | Cl | F | H | F | H | F | H |
| 172 | n-C$_3$H$_7$ | Cl | F | H | F | H | F | H |
| 173 | nC$_4$H$_9$ | Cl | F | H | F | H | F | H |
| 174 | n-C$_5$H$_{11}$ | Cl | F | H | F | H | F | H |
| 175 | n-C$_6$H$_{13}$ | Cl | F | H | F | H | F | H |
| 176 | H | Cl | H | H | F | H | H | H |
| 177 | CH$_3$ | Cl | H | H | F | H | H | H |
| 178 | C$_2$H$_5$ | Cl | H | H | F | H | H | H |
| 179 | n-C$_3$H$_7$ | Cl | H | H | F | H | F | H |
| 180 | nC$_4$H$_9$ | Cl | H | H | F | H | H | H |
| 181 | n-C$_5$H$_{11}$ | Cl | H | H | F | H | H | H |
| 182 | n-C$_6$H$_{13}$ | Cl | H | H | F | H | H | H |
| 183 | H | OCF$_3$ | H | H | H | H | H | H |
| 184 | CH$_3$ | OCF$_3$ | H | H | H | H | H | H |
| 185 | C$_2$H$_5$ | OCF$_3$ | H | H | H | H | H | H |
| 186 | n-C$_3$H$_7$ | OCF$_3$ | H | H | H | H | H | H |
| 187 | n-C$_4$H$_9$ | OCF$_3$ | H | H | H | H | H | H |
| 188 | n-C$_5$H$_{11}$ | OCF$_3$ | H | H | H | H | H | H |
| 189 | n-C$_6$H$_{13}$ | OCF$_3$ | H | H | H | H | H | H |
| 190 | H | OCF$_3$ | F | H | H | H | H | H |
| 191 | CH$_3$ | OCF$_3$ | F | H | H | H | H | H |
| 192 | C$_2$H$_5$ | OCF$_3$ | F | H | H | H | H | H |
| 193 | n-C$_3$H$_7$ | OCF$_3$ | F | H | H | H | H | H |
| 194 | n-C$_4$H$_9$ | OCF$_3$ | F | H | H | H | H | H |
| 195 | n-C$_5$H$_{11}$ | OCF$_3$ | F | H | H | H | H | H |
| 196 | n-C$_6$H$_{13}$ | OCF$_3$ | F | H | H | H | H | H |
| 197 | H | OCF$_3$ | F | F | H | H | H | H |
| 198 | CH$_3$ | OCF$_3$ | F | F | H | H | H | H |
| 199 | C$_2$H$_5$ | OCF$_3$ | F | F | H | H | H | H |
| 200 | n-C$_3$H$_7$ | OCF$_3$ | F | F | H | H | H | H |
| 201 | nC$_4$H$_9$ | OCF$_3$ | F | F | H | H | H | H |
| 202 | n-C$_5$H$_{11}$ | OCF$_3$ | F | F | H | H | H | H |
| 203 | n-C$_6$H$_{13}$ | OCF$_3$ | F | F | H | H | H | H |
| 204 | H | OCF$_3$ | F | F | F | H | H | H |
| 205 | CH$_3$ | OCF$_3$ | F | F | F | H | H | H |
| 206 | C$_2$H$_5$ | OCF$_3$ | F | F | F | H | H | H |
| 207 | n-C$_3$H$_7$ | OCF$_3$ | F | F | F | H | H | H |
| 208 | nC$_4$H$_9$ | OCF$_3$ | F | F | F | H | H | H |
| 209 | n-C$_5$H$_{11}$ | OCF$_3$ | F | F | F | H | H | H |
| 210 | n-C$_6$H$_{13}$ | OCF$_3$ | F | F | F | H | H | H |
| 211 | H | OCF$_3$ | F | F | F | F | H | H |
| 212 | CH$_3$ | OCF$_3$ | F | F | F | F | H | H |
| 213 | C$_2$H$_5$ | OCF$_3$ | F | F | F | F | H | H |
| 214 | n-C$_3$H$_7$ | OCF$_3$ | F | F | F | F | H | H |
| 215 | nC$_4$H$_9$ | OCF$_3$ | F | F | F | F | H | H |
| 216 | n-C$_5$H$_{11}$ | OCF$_3$ | F | F | F | F | H | H |
| 217 | n-C$_6$H$_{13}$ | OCF$_3$ | F | F | F | F | H | H |
| 218 | H | OCF$_3$ | F | F | F | F | F | H |
| 219 | CH$_3$ | OCF$_3$ | F | F | F | F | F | H |
| 220 | C$_2$H$_5$ | OCF$_3$ | F | F | F | F | F | H |
| 221 | n-C$_3$H$_7$ | OCF$_3$ | F | F | F | F | F | H |
| 222 | nC$_4$H$_9$ | OCF$_3$ | F | F | F | F | F | H |
| 223 | n-C$_5$H$_{11}$ | OCF$_3$ | F | F | F | F | F | H |
| 224 | n-C$_6$H$_{13}$ | OCF$_3$ | F | F | F | F | F | H |
| 225 | H | OCF$_3$ | F | F | F | F | F | F |
| 226 | CH$_3$ | OCF$_3$ | F | F | F | F | F | F |
| 227 | C$_2$H$_5$ | OCF$_3$ | F | F | F | F | F | F |
| 228 | n-C$_3$H$_7$ | OCF$_3$ | F | F | F | F | F | F |
| 229 | nC$_4$H$_9$ | OCF$_3$ | F | F | F | F | F | F |
| 230 | n-C$_5$H$_{11}$ | OCF$_3$ | F | F | F | F | F | F |
| 231 | n-C$_6$H$_{13}$ | OCF$_3$ | F | F | F | F | F | F |
| 232 | H | OCF$_3$ | F | F | F | H | F | H |
| 233 | CH$_3$ | OCF$_3$ | F | F | F | H | F | H |
| 234 | C$_2$H$_5$ | OCF$_3$ | F | F | F | H | F | H |
| 235 | n-C$_3$H$_7$ | OCF$_3$ | F | F | F | H | F | H |
| 236 | nC$_4$H$_9$ | OCF$_3$ | F | F | F | H | F | H |
| 237 | n-C$_5$H$_{11}$ | OCF$_3$ | F | F | F | H | F | H |
| 238 | n-C$_6$H$_{13}$ | OCF$_3$ | F | F | F | H | F | H |
| 239 | H | OCF$_3$ | F | F | H | H | F | H |
| 240 | CH$_3$ | OCF$_3$ | F | F | H | H | F | H |
| 241 | C$_2$H$_5$ | OCF$_3$ | F | F | H | H | F | H |
| 242 | n-C$_3$H$_7$ | OCF$_3$ | F | F | H | H | F | H |
| 243 | nC$_4$H$_9$ | OCF$_3$ | F | F | H | H | F | H |
| 244 | n-C$_5$H$_{11}$ | OCF$_3$ | F | F | H | H | F | H |
| 245 | n-C$_6$H$_{13}$ | OCF$_3$ | F | F | H | H | F | H |
| 246 | H | OCF$_3$ | F | H | F | H | H | H |
| 247 | CH$_3$ | OCF$_3$ | F | H | F | H | H | H |
| 248 | C$_2$H$_5$ | OCF$_3$ | F | H | F | H | H | H |
| 249 | n-C$_3$H$_7$ | OCF$_3$ | F | H | F | H | H | H |
| 250 | nC$_4$H$_9$ | OCF$_3$ | F | H | F | H | H | H |
| 251 | n-C$_5$H$_{11}$ | OCF$_3$ | F | H | F | H | H | H |
| 252 | n-C$_6$H$_{13}$ | OCF$_3$ | F | H | F | H | H | H |
| 253 | H | OCF$_3$ | H | H | F | H | H | H |
| 254 | CH$_3$ | OCF$_3$ | H | H | F | H | H | H |
| 255 | C$_2$H$_5$ | OCF$_3$ | H | H | F | H | H | H |
| 256 | n-C$_3$H$_7$ | OCF$_3$ | H | H | F | H | H | H |
| 257 | nC$_4$H$_9$ | OCF$_3$ | H | H | F | H | H | H |
| 258 | n-C$_5$H$_{11}$ | OCF$_3$ | H | H | F | H | H | H |
| 259 | n-C$_6$H$_{13}$ | OCF$_3$ | H | H | F | H | H | H |
| 260 | H | OCF$_3$ | F | H | F | H | F | H |
| 261 | CH$_3$ | OCF$_3$ | F | H | F | H | F | H |
| 262 | C$_2$H$_5$ | OCF$_3$ | F | H | F | H | F | H |
| 263 | n-C$_3$H$_7$ | OCF$_3$ | F | H | F | H | F | H |
| 264 | nC$_4$H$_9$ | OCF$_3$ | F | H | F | H | F | H |

-continued

| Example | R¹¹ | X¹¹ | L¹¹ | L¹² | L¹³ | L¹⁴ | L¹⁵ | L¹⁶ |
|---|---|---|---|---|---|---|---|---|
| 265 | n-C₅H₁₁ | OCF₃ | F | H | F | H | F | H |
| 266 | n-C₆H₁₃ | OCF₃ | F | H | F | H | F | H |
| 267 | H | OCF₃ | H | H | F | H | F | H |
| 268 | CH₃ | OCF₃ | H | H | F | H | F | H |
| 269 | C₂H₅ | OCF₃ | H | H | F | H | F | H |
| 270 | n-C₃H₇ | OCF₃ | H | H | F | H | F | H |
| 271 | nC₄H₉ | OCF₃ | H | H | F | H | F | H |
| 272 | n-C₅H₁₁ | OCF₃ | H | H | F | H | F | H |
| 273 | n-C₆H₁₃ | OCF₃ | H | H | F | H | F | H |
| 274 | H | OCHF₂ | H | H | H | H | H | H |
| 275 | CH₃ | OCHF₂ | H | H | H | H | H | H |
| 276 | C₂H₅ | OCHF₂ | H | H | H | H | H | H |
| 277 | n-C₃H₇ | OCHF₂ | H | H | H | H | H | H |
| 278 | n-C₄H₉ | OCHF₂ | H | H | H | H | H | H |
| 279 | n-C₅H₁₁ | OCHF₂ | H | H | H | H | H | H |
| 280 | n-C₆H₁₃ | OCHF₂ | H | H | H | H | H | H |
| 281 | H | OCHF₂ | F | H | H | H | H | H |
| 282 | CH₃ | OCHF₂ | F | H | H | H | H | H |
| 283 | C₂H₅ | OCHF₂ | F | H | H | H | H | H |
| 284 | n-C₃H₇ | OCHF₂ | F | H | H | H | H | H |
| 285 | n-C₄H₉ | OCHF₂ | F | H | H | H | H | H |
| 286 | n-C₅H₁₁ | OCHF₂ | F | H | H | H | H | H |
| 287 | n-C₆H₁₃ | OCHF₂ | F | H | H | H | H | H |
| 288 | H | OCHF₂ | F | F | H | H | H | H |
| 289 | CH₃ | OCHF₂ | F | F | H | H | H | H |
| 290 | C₂H₅ | OCHF₂ | F | F | H | H | H | H |
| 291 | n-C₃H₇ | OCHF₂ | F | F | H | H | H | H |
| 292 | nC₄H₉ | OCHF₂ | F | F | H | H | H | H |
| 293 | n-C₅H₁₁ | OCHF₂ | F | F | H | H | H | H |
| 294 | n-C₆H₁₃ | OCHF₂ | F | F | H | H | H | H |
| 295 | H | OCHF₂ | F | F | F | H | H | H |
| 296 | CH₃ | OCHF₂ | F | F | F | H | H | H |
| 297 | C₂H₅ | OCHF₂ | F | F | F | H | H | H |
| 298 | n-C₃H₇ | OCHF₂ | F | F | F | H | H | H |
| 299 | nC₄H₉ | OCHF₂ | F | F | F | H | H | H |
| 300 | n-C₅H₁₁ | OCHF₂ | F | F | F | H | H | H |
| 301 | n-C₆H₁₃ | OCHF₂ | F | F | F | H | H | H |
| 302 | H | OCHF₂ | F | F | F | F | H | H |
| 303 | CH₃ | OCHF₂ | F | F | F | F | H | H |
| 304 | C₂H₅ | OCHF₂ | F | F | F | F | H | H |
| 305 | n-C₃H₇ | OCHF₂ | F | F | F | F | H | H |
| 306 | nC₄H₉ | OCHF₂ | F | F | F | F | H | H |
| 307 | n-C₅H₁₁ | OCHF₂ | F | F | F | F | H | H |
| 308 | n-C₆H₁₃ | OCHF₂ | F | F | F | F | H | H |
| 309 | H | OCHF₂ | F | F | F | F | F | H |
| 310 | CH₃ | OCHF₂ | F | F | F | F | F | H |
| 311 | C₂H₅ | OCHF₂ | F | F | F | F | F | H |
| 312 | nC₄H₉ | OCHF₂ | F | F | F | F | F | H |
| 313 | nC₄H₉ | OCHF₂ | F | F | F | F | F | H |
| 314 | n-C₅H₁₁ | OCHF₂ | F | F | F | F | F | H |
| 315 | n-C₆H₁₃ | OCHF₂ | F | F | F | F | F | H |
| 316 | H | OCHF₂ | F | F | F | F | F | F |
| 317 | CH₃ | OCHF₂ | F | F | F | F | F | F |
| 318 | C₂H₅ | OCHF₂ | F | F | F | F | F | F |
| 319 | n-C₃H₇ | OCHF₂ | F | F | F | F | F | F |
| 320 | nC₄H₉ | OCHF₂ | F | F | F | F | F | F |
| 321 | n-C₅H₁₁ | OCHF₂ | F | F | F | F | F | F |
| 322 | n-C₆H₁₃ | OCHF₂ | F | F | F | F | F | F |
| 323 | H | OCHF₂ | F | H | F | H | F | H |
| 324 | CH₃ | OCHF₂ | F | H | F | H | F | H |
| 325 | C₂H₅ | OCHF₂ | F | H | F | H | F | H |
| 326 | n-C₃H₇ | OCHF₂ | F | H | F | H | F | H |
| 327 | nC₄H₉ | OCHF₂ | F | H | F | H | F | H |
| 328 | n-C₅H₁₁ | OCHF₂ | F | H | F | H | F | H |
| 329 | n-C₆H₁₃ | OCHF₂ | F | H | F | H | F | H |
| 330 | H | OCHF₂ | F | H | H | H | F | H |
| 331 | CH₃ | OCHF₂ | F | H | H | H | F | H |
| 332 | C₂H₅ | OCHF₂ | F | H | H | H | F | H |
| 333 | n-C₃H₇ | OCHF₂ | F | H | H | H | F | H |
| 334 | nC₄H₉ | OCHF₂ | F | H | H | H | F | H |
| 335 | n-C₅H₁₁ | OCHF₂ | F | H | H | H | F | H |
| 336 | n-C₆H₁₃ | OCHF₂ | F | H | H | H | F | H |
| 337 | H | OCHF₂ | F | H | H | F | H | H |
| 338 | CH₃ | OCHF₂ | F | H | H | F | H | H |
| 339 | C₂H₅ | OCHF₂ | F | H | H | F | H | H |
| 340 | n-C₃H₇ | OCHF₂ | F | H | H | F | H | H |
| 341 | nC₄H₉ | OCHF₂ | F | H | H | F | H | H |
| 342 | n-C₅H₁₁ | OCHF₂ | F | H | F | H | H | H |
| 343 | n-C₆H₁₃ | OCHF₂ | F | H | F | H | H | H |
| 344 | H | OCHF₂ | H | H | F | H | H | H |
| 345 | CH₃ | OCHF₂ | H | H | F | H | H | H |
| 346 | C₂H₅ | OCHF₂ | H | H | F | H | H | H |
| 347 | n-C₃H₇ | OCHF₂ | H | H | F | H | H | H |
| 348 | nC₄H₉ | OCHF₂ | H | H | F | H | H | H |
| 349 | n-C₅H₁₁ | OCHF₂ | H | H | F | H | H | H |
| 350 | n-C₆H₁₃ | OCHF₂ | H | H | F | H | H | H |
| 351 | H | OCHF₂ | F | H | F | H | F | H |
| 352 | CH₃ | OCHF₂ | F | H | F | H | F | H |
| 353 | C₂H₅ | OCHF₂ | F | H | F | H | F | H |
| 354 | n-C₃H₇ | OCHF₂ | F | H | F | H | F | H |
| 355 | nC₄H₉ | OCHF₂ | F | H | F | H | F | H |
| 356 | n-C₅H₁₁ | OCHF₂ | F | H | F | H | F | H |
| 357 | n-C₆H₁₃ | OCHF₂ | F | H | F | H | F | H |
| 358 | H | OCHF₂ | H | H | F | H | F | H |
| 359 | CH₃ | OCHF₂ | H | H | F | H | F | H |
| 360 | C₂H₅ | OCHF₂ | H | H | F | H | F | H |
| 361 | n-C₃H₇ | OCHF₂ | H | H | F | H | F | H |
| 362 | nC₄H₉ | OCHF₂ | H | H | F | H | F | H |
| 363 | n-C₅H₁₁ | OCHF₂ | H | H | F | H | F | H |
| 364 | n-C₆H₁₃ | OCHF₂ | H | H | F | H | F | H |
| 365 | H | CN | H | H | H | H | H | H |
| 366 | CH₃ | CN | H | H | H | H | H | H |
| 367 | C₂H₅ | CN | H | H | H | H | H | H |
| 368 | n-C₃H₇ | CN | H | H | H | H | H | H |
| 369 | n-C₄H₉ | CN | H | H | H | H | H | H |
| 370 | n-C₅H₁₁ | CN | H | H | H | H | H | H |
| 371 | n-C₆H₁₃ | CN | H | H | H | H | H | H |
| 372 | H | CN | F | H | H | H | H | H |
| 373 | CH₃ | CN | F | H | H | H | H | H |
| 374 | C₂H₅ | CN | F | H | H | H | H | H |
| 375 | n-C₃H₇ | CN | F | H | H | H | H | H |
| 376 | n-C₄H₉ | CN | F | H | H | H | H | H |
| 377 | n-C₅H₁₁ | CN | F | H | H | H | H | H |
| 378 | n-C₆H₁₃ | CN | F | H | H | H | H | H |
| 379 | H | CN | F | F | H | H | H | H |
| 380 | CH₃ | CN | F | F | H | H | H | H |
| 381 | C₂H₅ | CN | F | F | H | H | H | H |
| 382 | n-C₃H₇ | CN | F | F | H | H | H | H |
| 383 | nC₄H₉ | CN | F | F | H | H | H | H |
| 384 | n-C₅H₁₁ | CN | F | F | H | H | H | H |
| 385 | n-C₆H₁₃ | CN | F | F | H | H | H | H |
| 386 | H | CN | F | F | F | H | H | H |
| 387 | CH₃ | CN | F | F | F | H | H | H |
| 388 | C₂H₁₅ | CN | F | F | F | H | H | H |
| 389 | n-C₃H₇ | CN | F | F | F | H | H | H |
| 390 | nC₄H₉ | CN | F | F | F | H | H | H |
| 391 | n-C₅H₁₁ | CN | F | F | F | H | H | H |
| 392 | n-C₆H₁₃ | CN | F | F | F | H | H | H |
| 393 | H | CN | F | F | F | F | H | H |
| 394 | CH₃ | CN | F | F | F | F | H | H |
| 395 | C₂H₅ | CN | F | F | F | F | H | H |
| 396 | n-C₃H₇ | CN | F | F | F | F | H | H |
| 397 | nC₄H₉ | CN | F | F | F | F | H | H |
| 398 | n-C₅H₁₁ | CN | F | F | F | F | H | H |
| 399 | n-C₆H₁₃ | CN | F | F | F | F | H | H |
| 400 | H | CN | F | F | F | F | F | H |
| 401 | CH₃ | CN | F | F | F | F | F | H |
| 402 | C₂H₅ | CN | F | F | F | F | F | H |
| 403 | n-C₃H₇ | CN | F | F | F | F | F | H |
| 404 | nC₄H₉ | CN | F | F | F | F | F | H |
| 405 | n-C₅H₁₁ | CN | F | F | F | F | F | H |
| 406 | n-C₆H₁₃ | CN | F | F | F | F | F | H |
| 407 | H | CN | F | F | F | F | F | F |
| 408 | CH₃ | CN | F | F | F | F | F | F |
| 409 | C₂H₅ | CN | F | F | F | F | F | F |
| 410 | n-C₃H₇ | CN | F | F | F | F | F | F |
| 411 | nC₄H₉ | CN | F | F | F | F | F | F |
| 412 | n-C₅H₁₁ | CN | F | F | F | F | F | F |
| 413 | n-C₆H₁₃ | CN | F | F | F | F | F | F |
| 414 | H | CN | F | F | F | H | F | H |
| 415 | CH₃ | CN | F | F | F | H | F | H |
| 416 | C₂H₅ | CN | F | F | F | H | F | H |
| 417 | n-C₃H₇ | CN | F | F | F | H | F | H |
| 418 | nC₄H₉ | CN | F | F | F | H | F | H |

-continued

| Example | $R^{11}$ | $X^{11}$ | $L^{11}$ | $L^{12}$ | $L^{13}$ | $L^{14}$ | $L^{15}$ | $L^{16}$ |
|---|---|---|---|---|---|---|---|---|
| 419 | n-$C_5H_{11}$ | CN | F | F | F | H | F | H |
| 420 | n-$C_6H_{13}$ | CN | F | F | F | H | F | H |
| 421 | H | CN | F | F | H | H | F | H |
| 422 | $CH_3$ | CN | F | F | H | H | F | H |
| 423 | $C_2H_5$ | CN | F | F | H | H | F | H |
| 424 | n-$C_3H_7$ | CN | F | F | H | H | F | H |
| 425 | n$C_4H_9$ | CN | F | F | H | H | F | H |
| 426 | n-$C_5H_{11}$ | CN | F | F | H | H | F | H |
| 427 | n-$C_6H_{13}$ | CN | F | F | H | H | F | H |
| 428 | H | CN | F | H | F | H | H | H |
| 429 | $CH_3$ | CN | F | H | F | H | H | H |
| 430 | $C_2H_5$ | CN | F | H | F | H | H | H |
| 431 | n-$C_3H_7$ | CN | F | H | F | H | H | H |
| 432 | n$C_4H_9$ | CN | F | H | F | H | H | H |
| 433 | n-$C_5H_{11}$ | CN | F | H | F | H | H | H |
| 434 | n-$C_6H_{13}$ | CN | F | H | F | H | H | H |
| 435 | H | CN | H | H | F | H | H | H |
| 436 | $CH_3$ | CN | H | H | F | H | H | H |
| 437 | $C_2H_5$ | CN | H | H | F | H | H | H |
| 438 | n-$C_3H_7$ | CN | H | H | F | H | H | H |
| 439 | n$C_4H_9$ | CN | H | H | F | H | H | H |
| 440 | n-$C_5H_{11}$ | CN | H | H | F | H | H | H |
| 441 | n-$C_6H_{13}$ | CN | H | H | F | H | H | H |
| 442 | H | CN | F | H | F | H | F | H |
| 443 | $CH_3$ | CN | F | H | F | H | F | H |
| 444 | $C_2H_5$ | CN | F | H | F | H | F | H |
| 445 | n-$C_3H_7$ | CN | F | H | F | H | F | H |
| 446 | n$C_4H_9$ | CN | F | H | F | H | F | H |
| 447 | n-$C_5H_{11}$ | CN | F | H | F | H | F | H |
| 448 | n-$C_6H_{13}$ | CN | F | H | F | H | F | H |
| 449 | H | CN | H | H | F | H | F | H |
| 450 | $CH_3$ | CN | H | H | F | H | F | H |
| 451 | $C_2H_5$ | CN | H | H | F | H | F | H |
| 452 | n-$C_3H_7$ | CN | H | H | F | H | F | H |
| 453 | n$C_4H_9$ | CN | H | H | F | H | F | H |
| 454 | n-$C_5H_{11}$ | CN | H | H | F | H | F | H |
| 455 | n-$C_6H_{13}$ | CN | H | H | F | H | F | H |

MIXTURE EXAMPLE 1

| | | | |
|---|---|---|---|
| BCH-3F.F | 10.8% | Cl.p. [° C.]: | 102.2 |
| BCH-5F.F | 9.0% | Δn [589 nm; 20° C.] | +0.1097 |
| ECCP-30$CF_3$ | 4.5% | $\epsilon_\perp$ [1 kHz, 20° C.] | 3.3 |
| ECCP-50$CF_3$ | 4.5% | Δε [1 kHz, 20° C.] | +6.9 |
| CBC-33F | 1.8% | | |
| CBC-53F | 1.8% | | |
| CBC-55F | 1.8% | | |
| PCH-5F | 9.0% | | |
| PCH-6F | 7.2% | | |
| PCH-7F | 5.4% | | |
| CCP-20$CF_3$ | 7.2% | | |
| CCP-30$CF_3$ | 10.8% | | |
| CCP-40$CF_3$ | 6.3% | | |
| CCP-50$CF_3$ | 9.9% | | |
| APGU-3-F | 10.0% | | |

The invention claimed is:

1. Liquid-crystalline compound of the formula I where $R^{11}$ denotes H, an alkyl or alkoxy radical having 1 to 15 carbon atoms or alkenyl or alkenyloxy radical having 2 to 15 carbon atoms, each of which is unsubstituted or mono- or polysubstituted by halogen, where, in addition, one or more $CH_2$ groups in these radicals may each, independently of one another, be replaced by —C≡C—, —CH=CH—, —O—, —CO—O— or —O—CO— in such a way that O atoms are not linked directly to one another;

$X^{11}$ denotes F, Cl, CN, NCS, $SF_5$, halogenated alkyl radical, halogenated alkoxy radical, halogenated alkenyl radical or halogenated alkenyloxy radical, each having up to 7 C atoms, and $Z^{11}$ is a single bond, $Z^{12}$ and $Z^{13}$ each, independently of one another, denote —$C_2H_4$—, —C≡C—, —$C_2F_4$—, —CHO—, —OCH—, —COO—, —CF=CF—, —CH=CH—, —CH=CF—, —$CF_2$O—, —$OCF_2$—, —$(CH_2)_4$—, —$(CH_2)_3$— or a single bond, $L^{11}$, $L^{12}$, $L^{13}$, $L^{14}$, $L^{15}$ and $L^{16}$, independently of one another, denote H or F.

2. Compound according to claim 1, wherein $L^{14}$ and $L^{16}$ denote H.

3. Compound according to claim 1, wherein at least one of the substituents $L^{13}$ and $L^{15}$ denotes F.

4. Compound according to claim 1, wherein $L^{13}$ denotes F.

5. Compound according to claim 1, wherein $L^{11}$ and $L^{12}$ simultaneously denote F.

6. Compound according to claim 1, wherein $R^{11}$ denotes a straight-chain, unsubstituted alkyl or alkenyl radical having up to 7 carbon atoms.

7. Compound according to claim 1, wherein $X^{11}$ denotes F, $OCF_3$, $OCHF_2$ or CN.

8. Compound according to claim 1, selected from the group consisting of compounds of the formulae I1 to I27:

-continued

-continued

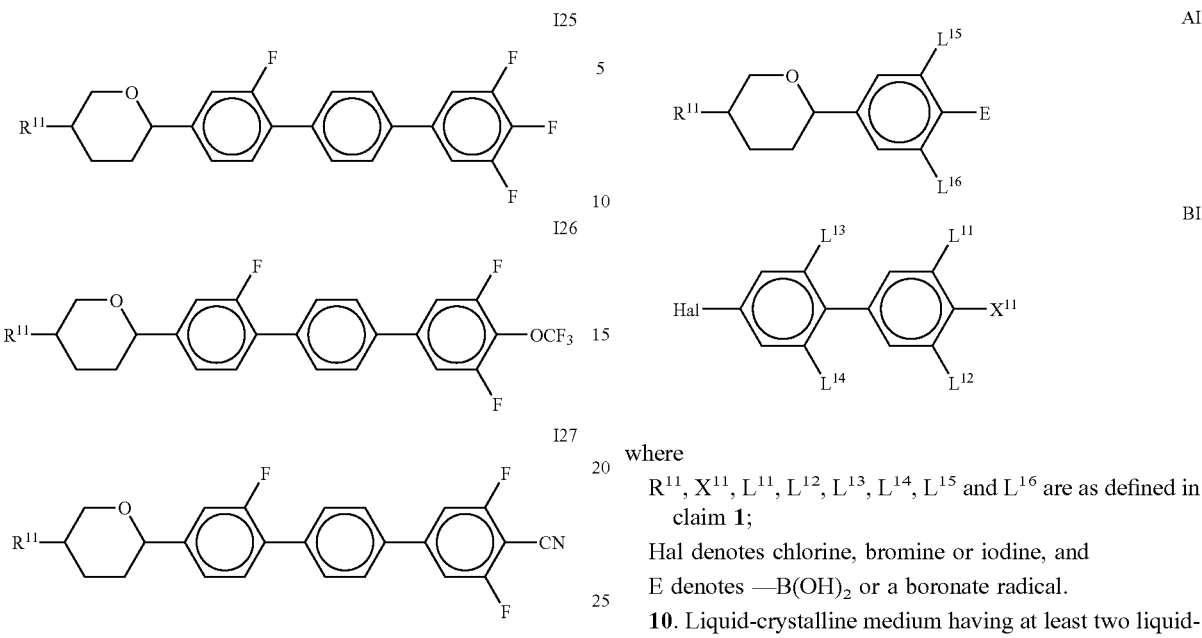

where R[11] is as defined in claim 1.

9. Process for the preparation of a compound of the formula I according to claim 1, a compound of the formula AI is reacted with a compound of the formula BI in the presence of a palladium complex catalyst:

where
 $R^{11}, X^{11}, L^{11}, L^{12}, L^{13}, L^{14}, L^{15}$ and $L^{16}$ are as defined in claim 1;
 Hal denotes chlorine, bromine or iodine, and
 E denotes —B(OH)$_2$ or a boronate radical.

10. Liquid-crystalline medium having at least two liquid-crystalline compounds, comprising at least one compound of the formula I according to claim 1.

11. Electro-optical liquid-crystal display containing a liquid-crystalline medium according to claim 10.

* * * * *

UNITED STATES PATENT AND TRADEMARK OFFICE
CERTIFICATE OF CORRECTION

PATENT NO. : 7,361,388 B2  Page 1 of 1
APPLICATION NO. : 10/558209
DATED : April 22, 2008
INVENTOR(S) : Peer Kirsch It is certified that error appears in the above-identified patent and that said Letters Patent is hereby corrected as shown below:

Column 63, line 31, reads "claim 1, a compound" should read --claim 1, wherein a compound--

Signed and Sealed this

Twenty-fifth Day of August, 2009

David J. Kappos
*Director of the United States Patent and Trademark Office*